United States Patent [19]

Lopez

[11] Patent Number: 5,694,686
[45] Date of Patent: Dec. 9, 1997

[54] METHOD FOR ASSEMBLING A MEDICAL VALVE

[75] Inventor: George A. Lopez, Corona del Mar, Calif.

[73] Assignee: ICU Medical, Inc., San Clemente, Calif.

[21] Appl. No.: 265,181

[22] Filed: Jun. 24, 1994

Related U.S. Application Data

[63] Continuation-in-part of Ser. No. 96,659, Jul. 23, 1993, which is a continuation-in-part of PCT/US92/10367, Dec. 1, 1992, which is a continuation-in-part of Ser. No. 813,073, Dec. 18, 1991, abandoned.

[51] Int. Cl.$^6$ .................................................. B23P 15/00
[52] U.S. Cl. ............................... 29/890.126; 29/890.132
[58] Field of Search ........................... 29/890.12 C, 428, 29/890.13, 890.132, 464, 469.5; 604/283

[56] References Cited

U.S. PATENT DOCUMENTS

| | | |
|---|---|---|
| 1,578,517 | 3/1926 | Hein . |
| 2,289,677 | 7/1942 | Perelson . |
| 3,852,385 | 12/1974 | Huggins . |
| 3,974,832 | 8/1976 | Kruck . |
| 3,976,073 | 8/1976 | Quick et al. . |
| 4,128,098 | 12/1978 | Bloom et al. . |
| 4,161,949 | 7/1979 | Thanawalla . |
| 4,187,846 | 2/1980 | Lolachi et al. . |
| 4,214,779 | 7/1980 | Losell . |
| 4,219,912 | 9/1980 | Adams . |
| 4,294,249 | 10/1981 | Sheehan et al. . |
| 4,296,949 | 10/1981 | Muetterties et al. . |
| 4,306,205 | 12/1981 | Svensson . |
| 4,328,802 | 5/1982 | Curley et al. . |
| 4,329,987 | 5/1982 | Rogers et al. . |
| 4,362,156 | 12/1982 | Feller, Jr. et al. . |
| 4,432,759 | 2/1984 | Gross et al. . |
| 4,439,188 | 3/1984 | Dennehey et al. . |
| 4,439,193 | 3/1984 | Larkin . |
| 4,511,359 | 4/1985 | Vaillancourt . |
| 4,564,054 | 1/1986 | Gustavsson . |
| 4,592,356 | 6/1986 | Gutierrez . |
| 4,645,494 | 2/1987 | Lee et al. . |
| 4,706,487 | 11/1987 | Bandou et al. . |
| 4,752,292 | 6/1988 | Lopez et al. . |

(List continued on next page.)

FOREIGN PATENT DOCUMENTS

| | | |
|---|---|---|
| 0114677 | 8/1984 | European Pat. Off. . |
| 0 237 321 | 3/1987 | European Pat. Off. . |
| 0240987 | 10/1987 | European Pat. Off. . |
| 0309771 | 4/1989 | European Pat. Off. . |
| 0 446 463 A1 | 12/1990 | European Pat. Off. . |
| 855319 | 11/1952 | Germany . |
| 84251972 | 9/1985 | Germany . |
| 8601712 | 3/1986 | WIPO . |
| WO93/11828 | 6/1993 | WIPO . |

*Primary Examiner*—Irene Cuda
*Attorney, Agent, or Firm*—Knobbe, Martens, Olson & Bear

[57] ABSTRACT

A closed system, needleless valve device includes a generally tubular body defining an internal cavity. On the proximal end of the body there is an opening which is preferably sufficiently large to receive an ANSI standard tip of a medical implement. The distal end of the body has a generally tubular skirt. The valve also includes a hollow spike having a closed tip. The spike includes at least one longitudinal 18-gauge hole located distal the tip, and is seated inside the cavity such that the tip is below the proximal end of the body. An annular support cuff is connected to the spike which seals off a portion of the cavity of the body such that an upper cavity containing the tip is defined. The valve also includes a plastic, resilient silicone seal which fills the upper cavity and opening and covers the tip of the spike so as to present a flush surface. An adaptor enables the valve to be attached to a resealable container. The valve is created by placing the spike with the seal thereon within the body. The spike and seal are preferably prevented from being removed from the body by at least one retaining tab that is created during assembly of the valve by gouging material from an inner surface of the body with a gouging bit as the valve is assembled.

7 Claims, 29 Drawing Sheets

U.S. PATENT DOCUMENTS

| | | |
|---|---|---|
| 4,781,702 | 11/1988 | Herrli . |
| 4,880,414 | 11/1989 | Whipple . |
| 4,889,527 | 12/1989 | Herrli . |
| 4,969,883 | 11/1990 | Gilbert et al. . |
| 4,998,921 | 3/1991 | Vickroy et al. . |
| 5,024,616 | 6/1991 | Ogle, II . |
| 5,069,225 | 12/1991 | Okamura . |
| 5,100,394 | 3/1992 | Dudar et al. . |
| 5,135,489 | 8/1992 | Jepson et al. . |
| 5,158,554 | 10/1992 | Jepson et al. . |
| 5,167,648 | 12/1992 | Jepson et al. . |
| 5,171,234 | 12/1992 | Jepson et al. . |
| 5,188,620 | 2/1993 | Jepson et al. . |
| 5,273,533 | 12/1993 | Bonaldo . |
| 5,344,414 | 9/1994 | Lopez et al. . |
| 5,401,245 | 3/1995 | Haining . |

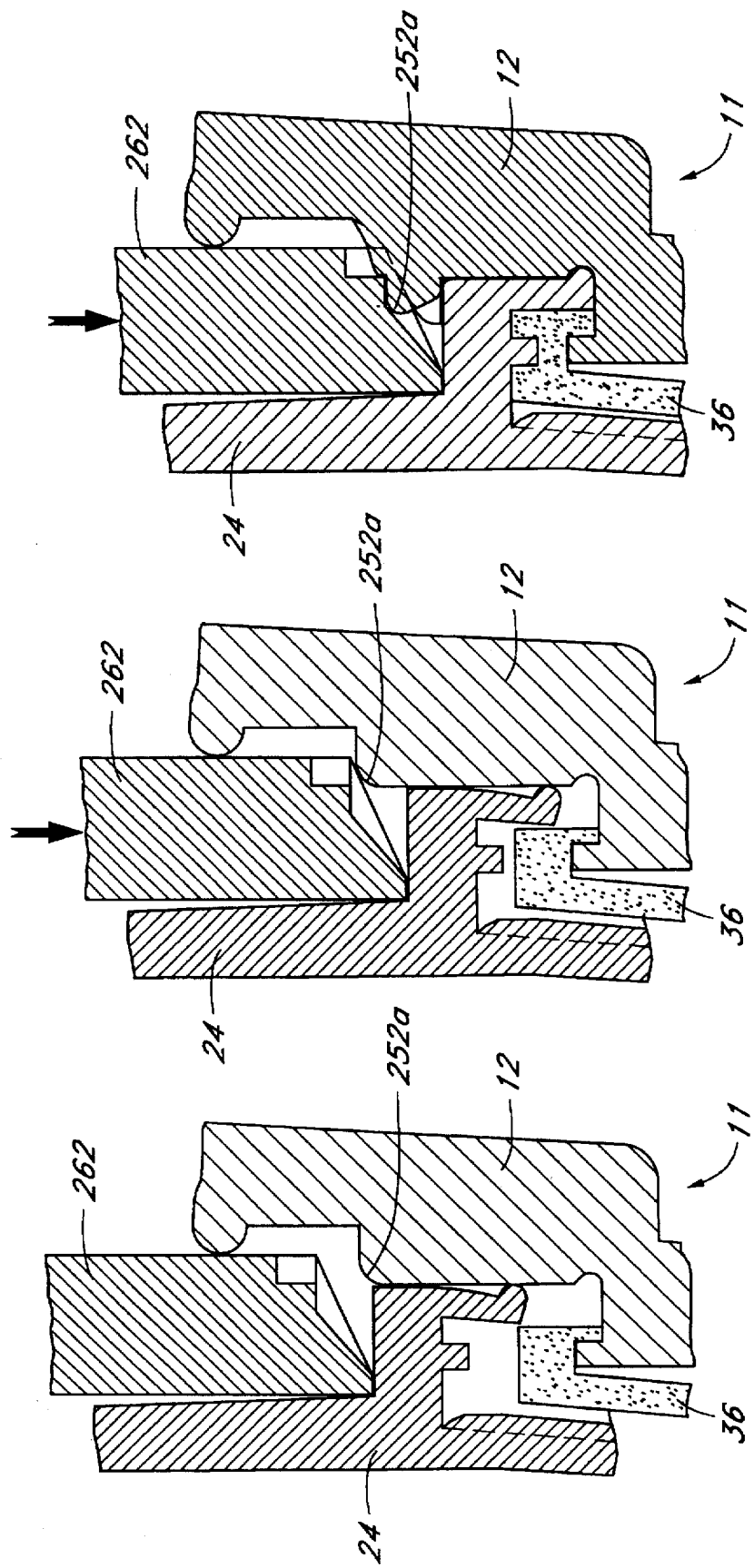

METHOD FOR ASSEMBLING A MEDICAL VALVE

RELATED APPLICATIONS

This application is a continuation-in-part of U.S. patent application Ser. No. 08/096,659, filed Jul. 23, 1993, which is a continuation-in-part application of PCT application Ser. No. PCT/US92/10367, filed Dec. 1, 1992, which designates the United States which is a continuation-in-part in the United States of U.S. patent application Ser. No. 07/813,073, filed Dec. 18, 1991, which is abandoned. The disclosures of these related applications are incorporated herein in their entirety by this reference thereto.

BACKGROUND OF THE INVENTION

1. Field of the Invention

This invention relates to a closed, patient access system which automatically reseals after administering medication using a standard medical implement that directly connects with the system without the need of any intermediary needles, caps or adaptors. A two-way valve eliminating dead space is used which includes a seal which, upon being compressed by the medical implement, is pierced to open the valve and reseals upon being decompressed, maintaining a fluid tight seal even at high pressures and after repeated uses.

2. Background Discussion

The manipulation of fluids for parenteral administration in hospital and medical settings routinely involves the use of connectors and adaptors for facilitating the movement of fluids between two points. Most fluid connectors and adaptors employ needles to pierce a septum covering sterile tubing or to pierce the septum of a medicament container of fluid. Fluid then passes from the container or fluid filled tubing into a syringe or second set of tubing. These connectors and adaptors often have mechanical or moving parts. Since the ready passage of fluids through the connectors and adaptors is often critical to patient survival, it is imperative that the connectors and adaptors function reliably and repeatedly. Adaptors and connectors that malfunction during use may be life-threatening. The more mechanical or moving parts such as springs and diaphragms, the more likely that they will function improperly. Improper functioning can result in the introduction of air embolisms into a patient. Thus, the fewer the mechanical parts, the more these connectors can be relied on and the better they will be accepted by the medical community.

Many connectors or valves, especially those employing several mechanical components, have a relatively high volume of fluid space within them. This "dead space" within the device prevents accurate introduction of precise fluid volumes and provides an opportunity for contamination upon disconnection of the device. Connectors and adaptors often include valves that permit or interrupt the flow of fluid along the course of fluid travel. Several of those commonly in use employ metal needles to puncture sterile seals. Such connectors are generally designed to accommodate fluid flow in one direction. This means that the fluid line must have connectors and tube aligned in complementary directions. These connectors often require further manipulation if, for example, the valve is inadvertently assembled in a direction that will not facilitate fluid flow. These manipulations increase handling, thereby increasing both the risk of contamination and the amount of time required to establish the fluid connection.

Metal needles employed as part of connector devices increase the risk of puncture wounds to the user. The needles used in these devices often have through-holes placed at the tip of the needle. Connection of the valve with a flow line involves piercing the needle through a sealed septum. Through-holes placed at the needle tip can core the septum and release free particulates into the flow line. Such an event can prove fatal to a patient. Such through-holes may also become clogged easily with material from the septum.

Reusable connectors and adaptors are preferred for medical applications since components must often be added or removed from a fluid line connected to a patient. Reusable connectors, however, are difficult to keep sterile. Sometimes caps are employed to cover the connector to keep it sterile. Frequently, these caps are lost, or simply not used because they are not readily available when needed.

A closed, patient access system that is easy to use and employs only a valve device in communication with the patient that need not be capped or interconnected with the medical implement through a needle or adaptor, is swabbable, is sufficiently durable to maintain its function after several manipulations, and maintains a fluid-tight seal at high pressures, would be of great benefit to the medical community.

SUMMARY OF THE INVENTION

The valve of this invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENTS," one will understand how the features of this invention provide its advantages, which include safety, reliable and repeatable performance, elimination of dead space, simplicity of manufacture and use, and employment of a valve that is swabbable after use to provide sterility and has a fluid-tight seal at high pressure.

This invention is a closed, patient access system which automatically reseals after administering medication using a medical implement that directly connects with the system without the need of any intermediate needles, caps or adaptors. A two-way valve is employed utilizing a reusable seal that may be repeatedly pierced by an enclosed, protected, non-metallic spike rather than an exposed metal needle. The valve facilitates fluid, particularly liquid, transfer while maintaining sterility. The valve is easy to use and is capable of locking in place. After use, the valve is swabbed in the conventional manner with a suitable substance to maintain sterility. The design of the valve avoids accidental needle sticks. As will be discussed in detail below, the valve is useful as a medical connector or adaptor to enable liquid flow from a sealed container.

The first feature of this invention is that the valve has a body including wall structure defining an internal cavity having a proximal end and a distal end. The cavity has an open space into which the seal is pushed, and preferably has a plurality of radial indentations in the wall structure that are adjacent the seal to accommodate the expansion of the seal upon compression. The proximal end has an opening sufficiently large to receive a delivery end of a medical implement which transfers fluid through the delivery end. In most applications, the delivery end of the implement is tapered, and the wall structure adjacent the opening is tapered inward so that the wall structure and the tapered delivery end fit snug against each other upon insertion of the delivery end into the opening. The proximal end of the cavity preferably is adapted to fit snug with an ANSI (American National Standards Institute, Washington, D.C.) standard end of the medical implement. Typically, the implement is a syringe, a connector or inlet/outlet of an IV set, or any one of a wide variety of conduits used in medical applications.

The second feature is that the spike has a tip with at least one hole located at or near the tip, and a passageway in communication with the hole that allows fluid to flow through this hole. The spike is seated inside the cavity such that the tip is inward of the proximal end and is enclosed within the cavity. Preferably, the hole is in a side of the spike adjacent the tip and is elongated, having a size of 18 gauge or greater. The tip may be sharp or slightly rounded. More than one hole is desirable for many applications, and three, symmetrically located holes inward of the proximal end are preferred. The spike may include at least one rib which allows air to enter a space between the seal and the spike, thereby facilitating the sealing of the opening when the implement is removed. The spike may have a substantially conical shape, and the seal has a complementarily, substantially conical shaped cavity within it conforming to the shape of the spike. The spike is disposed within this conical cavity and the seal covers the tip. The tip may be imbedded in the proximal end of the seal or withdrawn into the conical cavity. Preferably, the tip of the spike has a plurality of facets which meet within a recess. The preferred spike should be able to penetrate the seal repeatedly without tearing the seal. Rough edges at the tip may present a tear problem. During injection molding of the preferred plastic spike, facets of the tip will abut along a "parting line," and could form a rough edge which may tear the seal. This problem is avoided where the parting line is buried in a recess. Any rough edge at this parting line is disposed within a recess, so the seal material moves over the recess and does not contact the rough edge.

The third feature is that the resilient seal is adapted to be moved into a compressed state upon insertion of the tip of the medical implement into the opening and returns to a decompressed state upon removal of the tip. The seal in the decompressed state has a section which fills essentially completely a portion of the cavity adjacent the opening. The seal section bears against the wall structure near the opening to seal the opening. In the compressed state, the seal section is pushed by the delivery end of the medical implement away from the opening and into the cavity. A fluid tight seal is maintained between the seal section and the wall structure as the seal is moved into the compressed state. The seal section bears against the wall structure as the seal is moved inward into the cavity by the tip of the medical implement. And most importantly, the delivery end and the seal are adapted to engage so that when the tip of the spike pierces the seal there is essentially no dead space between the delivery end and the seal. Consequently, a predetermined dosage amount of medication is transferred in its entirety to the patient using this invention, with none of the prescribed amount being collected in dead space in the valve. The delivery of an exact amount of medication may be critical in some situations when chemotherapeutic agents are being administered or small children are being treated.

A fluid tight seal is maintained over repeated opening and closing of the valve, and the seal has on its external surface a recess which provides an air pocket to facilitate the movement of the seal. Preferably, the seal presents an essentially flush surface with the proximal end of the cavity. In one embodiment, the proximal end of the seal is substantially flat, the seal is made of a material having a hardness of from 30 to 70 Shore units such as, for example, a silicone polymer. The seal may include a cup-like flange adapted to engage the body near the proximal end of the cavity. A preferred embodiment of the seal comprises a series of O-ring elements stacked together and connected to form a unitary structure. The O-ring elements have increasing diameters, with the smallest diameter element being adjacent the proximal end of the cavity. The proximal end of the seal may be precut to form a tiny orifice therein that allows the tip of the spike to pass therethrough easily upon compression of the seal. Preferably, the proximal end of the seal has a truncated conical shaped segment disposed within the cavity. The seal may also have a centrally located, anti-vacuum, saucer like depression therein, which does not interfere with the ability of the exposed, proximal end of the seal being swabbed when desired.

The fourth feature is that the body and spike are two separate components of the valve that are securely attached to each other by assembly of, and interlocking, of the body and spike. The body has a first locking element near the distal end of the cavity, and the spike has a second locking element adapted to interlock with said first locking element upon assembly. The seal has a lip extending beyond the distal end and positioned between the first and second locking elements so that, upon assembly, the lip is compressed between the locking elements to provide an essentially fluid tight seal upon interlocking.

The fifth feature is that the medical valve may include a support member connected to the spike which seals off the distal end of the cavity. The support member may have a Luer-Lock type connector element that enables the valve to be removably attached to, for example, a fluid line connected to a patient. The support member may also be in the form of an adaptor that enables the valve to be removably attached to a fluid dispenser or container. When used to dispense fluids from a container, the spike has a pair of opposed tips, respectively at the distal and proximal ends of the spike. The tip at the distal end of the spike pierces a cover member which seals the container. A radial slit on the adaptor enables it to deform reversibly sufficiently to fit snugly onto said container.

The sixth feature is that the seal has a proximal end including a pressure responsive element disposed on an inner surface of the seal adjacent the opening. The pressure responsive element in the decompressed state closes any orifice in the seal at the proximal end of the seal to provide an essentially fluid-tight seal while in the decompressed state. The pressure responsive element enables the valve to maintain a fluid-tight seal even at very high pressures sometimes experienced in medical applications, particularly when the valve is connected to a patient's artery. The valve of this invention will remain closed even when the pressure inside the valve is above 6 pounds per square inch (psi), and it can withstand pressures above 30 psi. Typically, the pressure responsive element is a section of the seal having an entryway into a precut orifice. This section has a substantially cylindrical configuration and is surrounded by an annular space which is filled with pressurized fluid. The center of the member and the annular space are coaxial with the entryway to the orifice. The pressurized fluid fills the annular space to apply pressure that compresses the cylindrical section to tightly close the entryway to the orifice. Preferably, the pressure responsive element has an anti-tear element.

The seventh feature is that the body of a preferred embodiment of the present invention include one or more retaining tabs that secure the spike and the seal inside the body. The retaining tabs are preferably created by gouging a portion of the inside surface of the body and folding this material against a surface of the spike to confine the spike and seal between the retaining tabs and another surface of the body. The resultant retaining tab is rigid enough to hold the spike and seal tightly enough against the inner surfaces of the body to prevent fluid leakage. Creating these retaining tabs to secure the spike and seal inside the body increases the allowable tolerance between the body and the spike, which, consequently, minimizes the likelihood that the valve will leak fluid, while reducing the pressure created by the interference fit between the spike and the body. This pressure is often referred to as "hoop stress". Reducing hoop stress prevents the body from cracking, even during transmission of fats. A preferred method and apparatus for creating the retaining tabs, while assembling the valve is also disclosed below. This method and apparatus provide a quick, easy, inexpensive, and reliable method for assembling the valve.

In accordance with this invention, a known, prescribed, predetermined amount or dosage of medication may be transferred from the remote source to the patient directly, so that essentially none of the predetermined amount is collected in dead space in the valve. In other words, essentially all the prescribed dosage is received by the patient and not lost in the valve. Thus, this invention also includes a method of transferring fluid from a remote source to a patient. This invention also includes transfer of fluid from the patient to a remote source. This is possible because the valve of this invention provides two-way communication. The fluid is transferred to the patient by applying pressure to the fluid as it passes through the implement so that the pressure applied to the fluid is greater than the pressure of fluid in the patient, enabling transfer from the remote source to the patient. To achieve transfer of fluid from the patient to the remote source, the pressure of fluid in the patient is greater than the pressure at the remote source, causing fluid to flow from the patient to the remote source. This invention also includes a method of transferring fluid in a container having an open mouth covered by a cover member which seals the open mouth. The fluid is caused to flow from the container through the passageway by creating a differential in pressure. Preferably, the valve has an adaptor having a radial slit for allowing the adaptor to deform reversibly sufficiently to fit snugly onto said container.

BRIEF DESCRIPTION OF THE DRAWING

The preferred embodiments of this invention, illustrating all its features, will now be discussed in detail. These embodiments depict the novel and non-obvious method and valve of this invention shown in the accompanying drawing, which is for illustrative purposes only. This drawing includes the following Figures, with like numerals indicating like parts:

FIG. 33 is a close-up taken through line S—S of FIG. 32, just prior to the gouging bit deforming the gouging surface.

FIG. 34 is a close-up taken through line S—S of FIG. 32, as the gouging bit contacts the gouging surface.

FIG. 35 is a close-up view taken through line S—S of FIG. 32, just after the gouging bit has deformed the gouging surface.

DETAILED DESCRIPTION OF THE PREFERRED EMBODIMENTS

Figure 7:
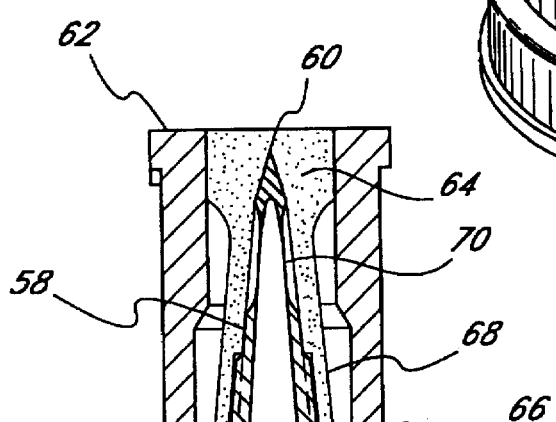
FIG. 7 is a longitudinal cross-sectional view of the valve of FIG. 6.
Figure 7:
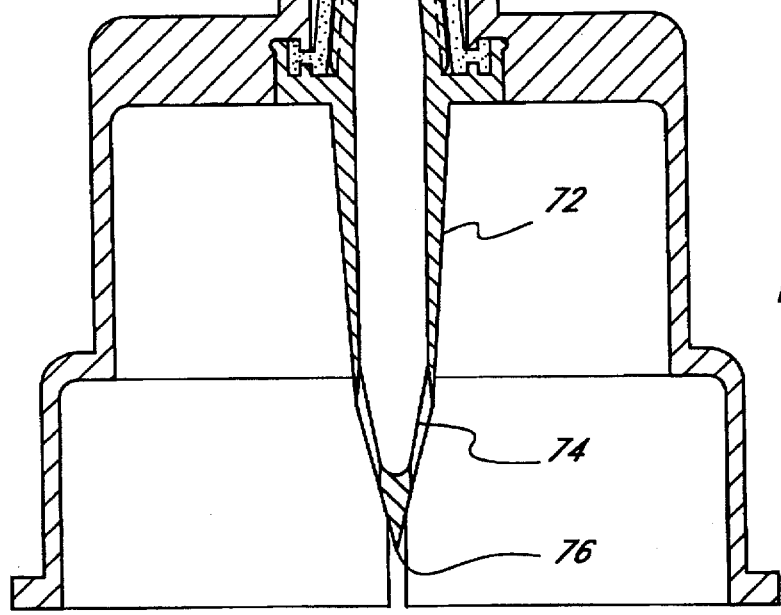

The term "proximal" is used to denote the end of the valve and other components at or near the spike tip 32 in FIGS. 2 through 5, 10 through 12, 14, 16 and 25, and at or near the spike tip 60 in FIG. 7, and at or near the seal cap 92 in FIGS. 8, 9 and 13 through 19. The term "distal" is used to denote the opposite end of the valve, or spike tip, or seal. The term "medical implement" is used to denote any medical tool known to those of skill in the art that can connect to the present invention and facilitate the passage of fluids, particularly liquids, through the instant invention. Examples of medical implements that are contemplated include, but are not limited to, tubing, conduit, syringes, IV sets (both peripheral and central lines), piggyback lines, and other components which can be used in connection with a medical valve. Medical implements are commercially available in standard sizes. Thus, either or both ends of the valve of this invention can be provided with fittings to accommodate such standard size medical implements.

Figures 1, 2:
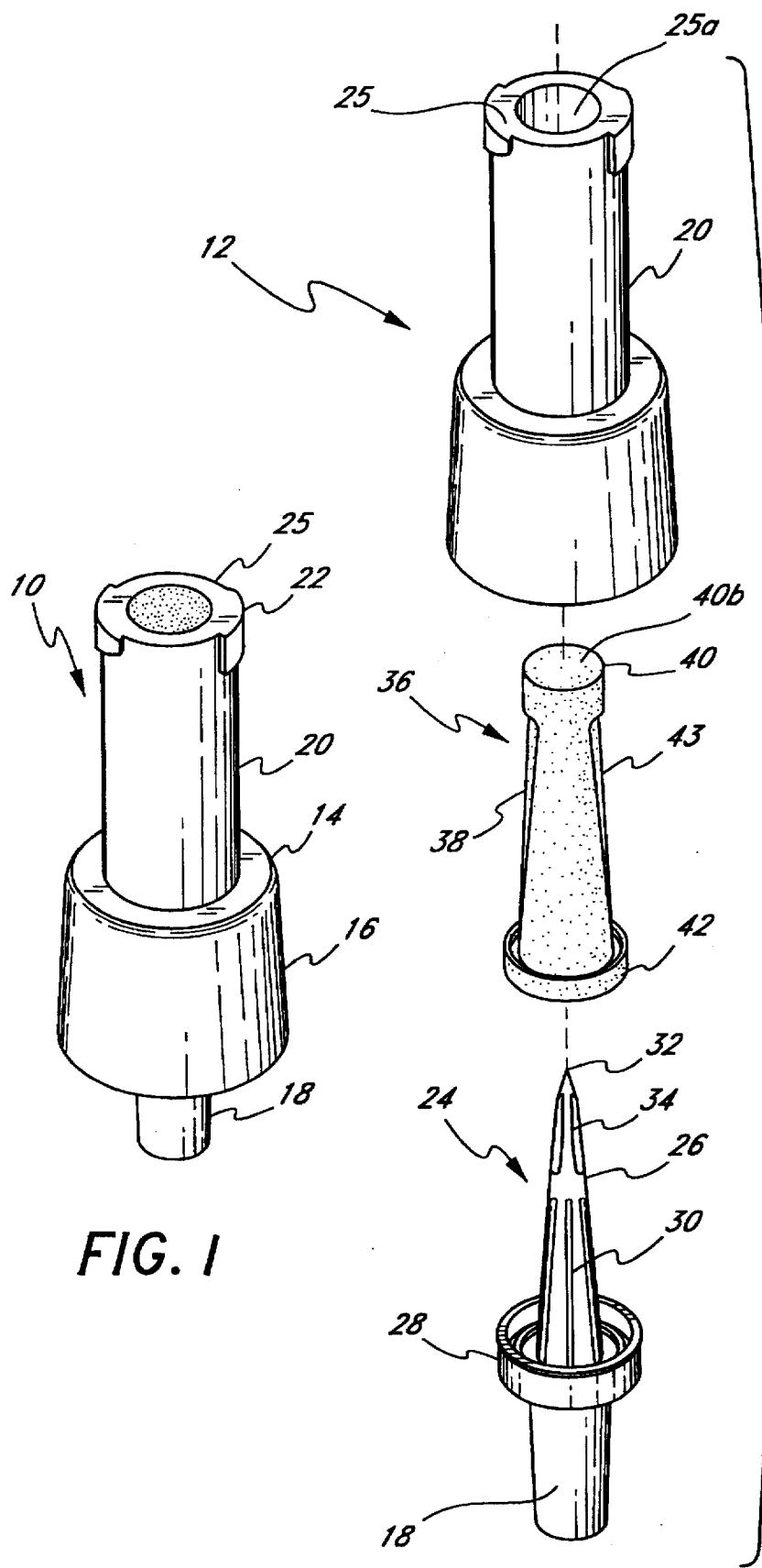
FIG. 1 is a perspective view of the first embodiment of the valve of this invention.
FIG. 2 is an exploded perspective view of the valve shown in FIG. 1 illustrating the spike, seal, and the body or housing components of the invention.
Figure 13:
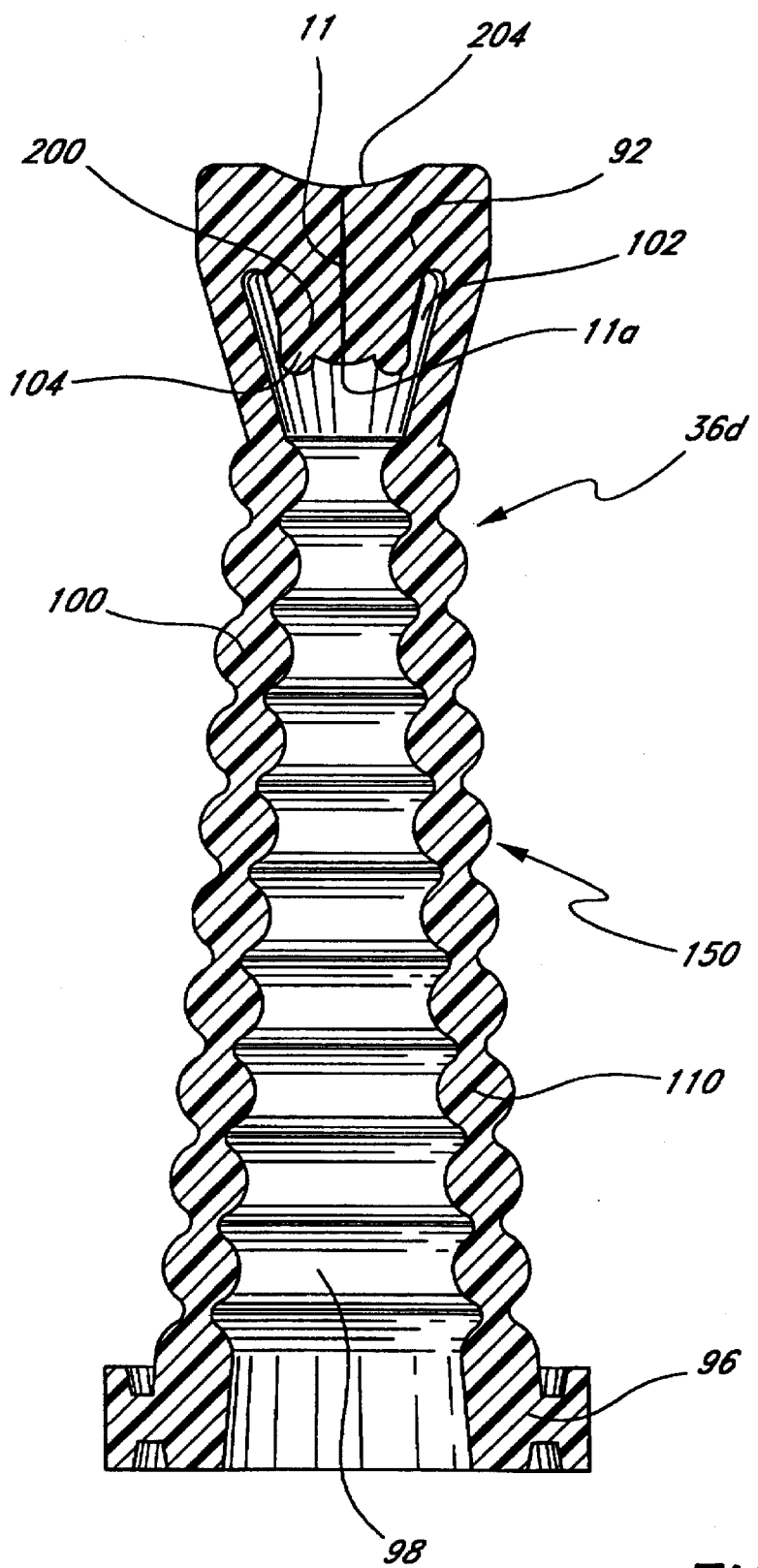
FIG. 13 is a longitudinal cross-sectional view of a sixth embodiment of the seal.

As best shown in FIGS. 1 and 2, the first embodiment of the invention, valve 10, includes a valve body or housing 12, a spike element 24, and a seal 36. The seal 36 is prepared from a resilient material that is flexible, inert, impermeable to fluid, and readily pierceable by the spike 26. In the embodiment shown in FIG. 13 depicting an alternate shaped seal 36d, this seal 36d has a precut slit 11 in its proximal end. This provides a tiny orifice through which the tip 32 of the spike element 24 may easily pass, yet still provides a fluid tight seal upon withdrawal of the spike element. In this embodiment, the spike element 24 can readily pierce the seal 36d through the precut slit 11.

Figure 3:
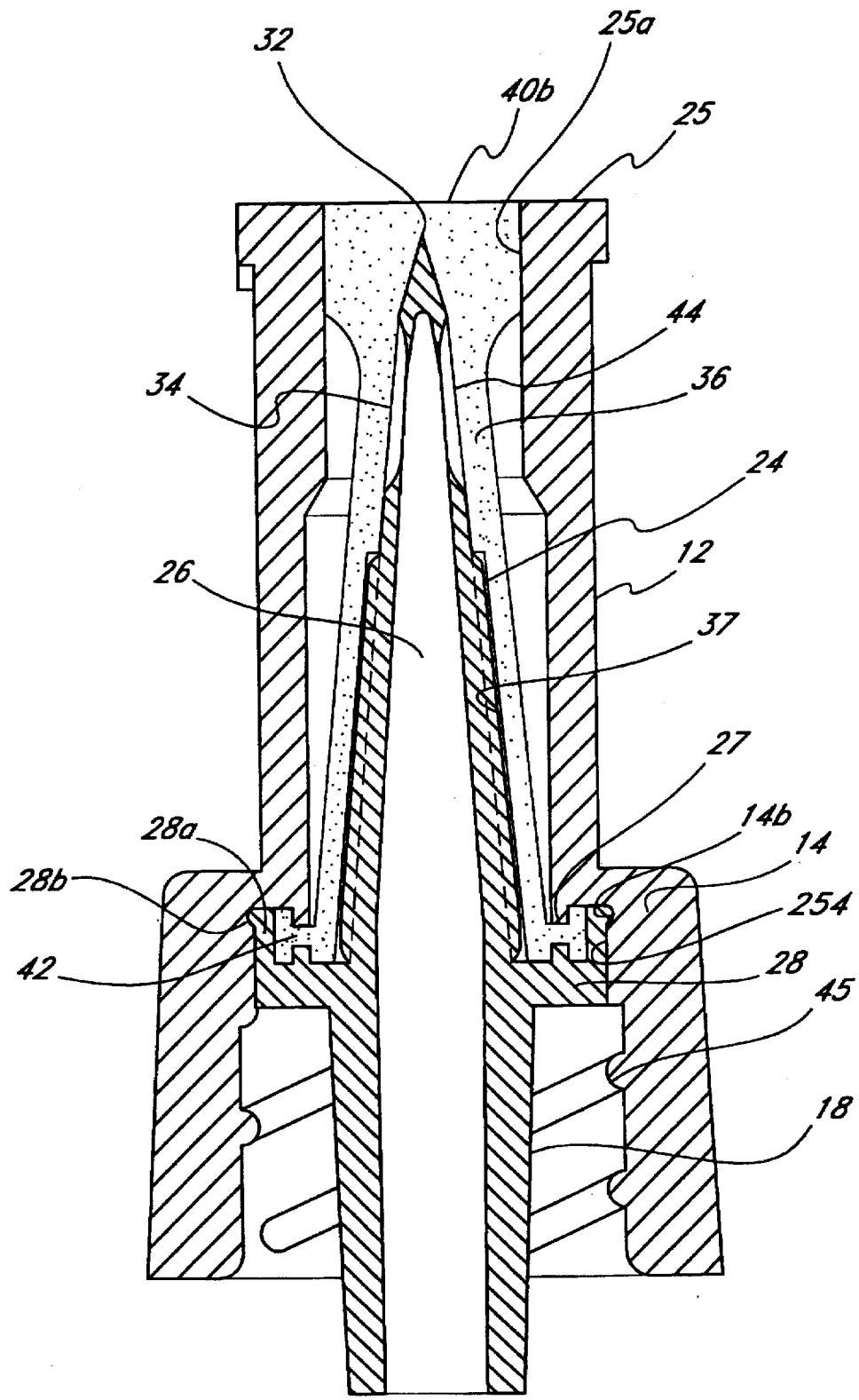
FIG. 3 is a longitudinal cross-sectional view of the valve of FIG. 1, after assembly by a first assembly method.
Figure 4:
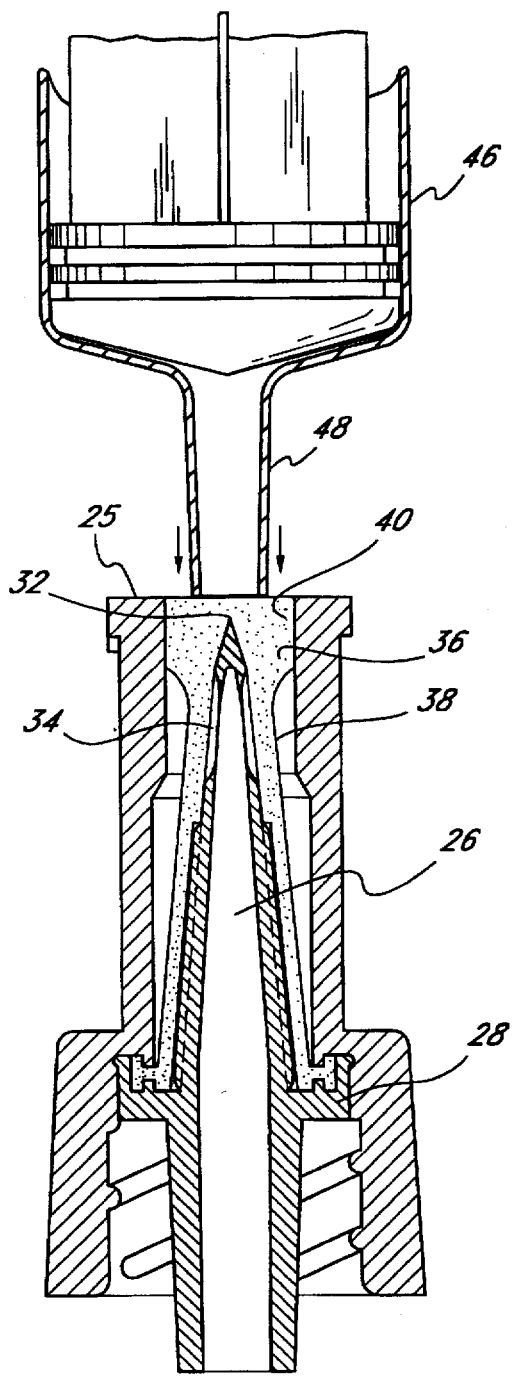
FIG. 4 is a schematic, longitudinal, cross-sectional view of the assembled valve of FIG. 1 before compressing the seal.
Figure 5:
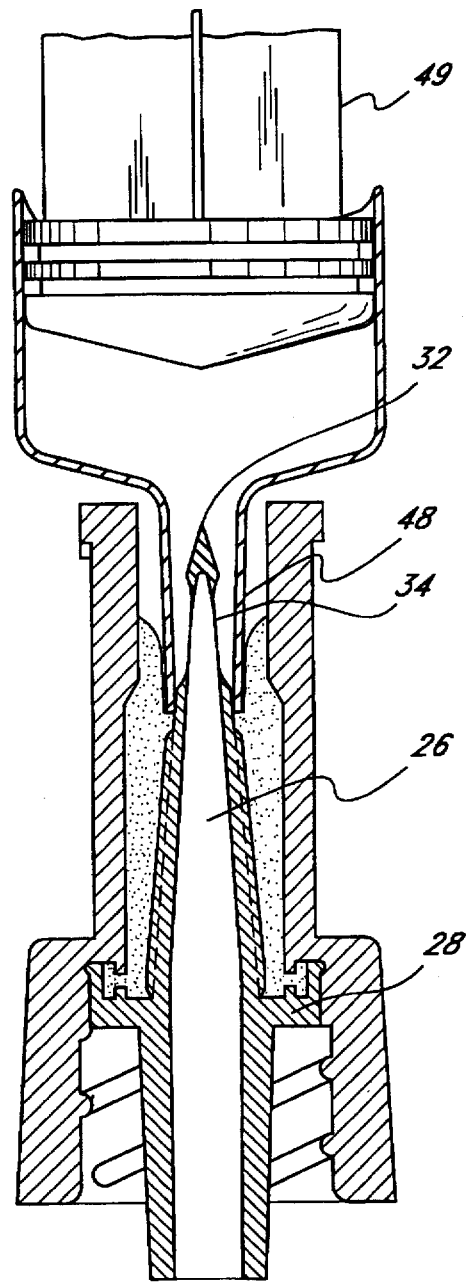
FIG. 5 is a schematic, longitudinal, cross-sectional view similar to FIG. 4 showing the valve during compression of the seal.

The housing 12, spike element 24, and seal 36 are assembled, as depicted in FIG. 3, for example, with the spike element 24 enclosed to prevent accidental sticks. FIG. 2 illustrates how the housing 12, seal 36, and spike element 24 are attached without the need to use any adhesive or other bonding agent or process. Mechanical connection which provides a fluid tight closure is attained as is discussed subsequently. As shown in FIGS. 4 and 5, the seal 36 moves within the housing 12, being pierced by the spike element 24 to expose the tip 32 of the spike element 24 to allow fluid to flow through the valve 10. The valve is often used in connection with fluids that are liquids, such as in the administration of medications intravenously. However, non-liquid fluids, such as air or other gases can also be accommodated through the valve.

Referring to FIG. 1, one preferred embodiment of housing 12 has a bell-shaped skirt 16 and an upper, preferably cylindrical, conduit 20. The skirt 16 is integral with, and connected by an annular ring 14 to the upper conduit 20. The skirt 16 creates a shield for an inner conduit 18 of the spike element 24. This inner conduit 18 is preferably cylindrical in shape, and slightly tapered. Inner conduit 18 and upper conduit 20 comprise aligned hollow tubes so that inner conduit 18 and upper conduit 20 are in fluid communication with one another when the spike element 24 pierces the seal 36. There is an annular lip 25 surrounding a circular opening 25a in the top of the conduit 20 (see FIG. 2).

In the first embodiment, the upper conduit 20 is adapted to receive the tip or nose 48 of an ANSI standard syringe 46 (see FIGS. 4 and 5). It is, however, contemplated that the outer diameter of the upper conduit 20 can be of any size to accommodate the attachment of other connector devices thereto. Advantageously, the proximal end of the upper conduit 20 can be equipped with a locking mechanism to facilitate locking of the valve 10 to a variety of connector devices. For example, referring to FIG. 1, locking ears 22 near the proximal lip 25 of housing 12 are preferably provided such that the housing 12 can be locked into any compatible Luer-Lock device known to those with skill in the art. For example, referring to FIG. 19, conventional Luer-Lock threads 180 can be provided on the outer diameter of upper conduit 20.

Referring to FIG. 2, the spike element 24 has at its distal end the inner conduit 18 and at its proximal end a hollow spike 26 which is integral with the inner conduit. The spike 26 is shown in an elongated form. However, one having ordinary skill in the art will recognize that shorter, more rounded spikes can also be used for this purpose. The inner conduit 18 and spike 26 present a continuous passageway for fluid during use. An annular cuff 28 on an intermediate portion of the spike element 24 is integral with, and interconnects, the inner conduit 18 and the spike 26. As illustrated in FIG. 3, the rim 28a of the cuff 28 abuts the underside of the inner ring 14, and has an annular detent 28b that snaps into an annular groove 14b in the underside of the ring. The cuff 28 serves two functions. First, it serves as an attachment device to the underside of the annular ring 14. Second, it serves as a support and attachment device for the seal 36.

The hollow spike 26 has a tapered conical shape, ending in a sharp, pointed tip 32. Preferably, along the length of the spike are raised, protruding ridges 30. These raised ridges 30 extend from the surface of the spike preferably between 0.2–2.0 mm. The ridges 30 are preferably aligned along the length of the spike as illustrated in FIG. 2. These ridges 30 serve to break any vacuum created when the spike 26 is sealed as described hereinbelow. Modifications to the alignment and orientation of the ridges are discussed hereinbelow in association with their function. Just distal the spike tip 32, there is situated at least one longitudinal through-hole 34 to permit fluid communication between the inner conduit 18 and the upper conduit 20. Preferably, there are three through-holes 34 within about 0.200 inch from the spike tip 32. These through-holes 34 may be of any size, however, the larger the size of the through-holes the greater the fluid flow rate through the valve 10. In a preferred embodiment, the size of the through-holes 34 are 18-gauge to provide a flow rate three times that of a standard 18 gauge needle. The through-holes can also take the form of the pores in a porous or mesh material, such as a spongy material or membrane. In the case of such porous or mesh materials there are a large number of very small through-holes present.

The seal 36 has a seal cap 40 with a generally flat top surface 40b, an outwardly tapered sidewall 38, and a lower lip 42. Its interior is hollow to provide the conically shaped cavity 37 (FIG. 3). Thus, the seal 36 slips easily over the spike element 24 to fit snugly within the cavity 37. The seal lip 42 is seated within the annular cuff 28 and wedged between the cuff and the underside of the ring 14. There are longitudinal grooves 43 (FIG. 2) along the length of the seal 36 which provide air pockets that facilitate compression of the seal 36 during use. The grooves 43 may be of variable shape or size to facilitate seal compression. In the first embodiment, there is a single groove 43 which completely surrounds the seal 36 between the seal cap 40 and the lip 42.

The base of the seal 36 has a width such that the seal lip 42 fits snugly into the annular cuff 28 The hollow interior or cavity 37 (FIG. 3) of the seal 36 is preferably tapered to conform internally to the shape of the spike 24, having a wall portion 44 which contacts the spike 24 distal the seal cap 40. The exterior of the seal 36 is sized and shaped to fit inside the upper conduit 20 of the housing 12. The cap 40 reseals the valve 10 when the top surface 40b is above the through-holes 34. Preferably, the cap 40 substantially fills the opening 25a in the top of the conduit 20. Thus, after assembly, the top surface 40b of the seal cap 40 is essentially flush with the lip 25, so that the lip 25 and seal cap 40 can be swabbed with alcohol or other disinfectant without leakage of disinfectant into the valve 10. It is important that the surface 40b be exposed so that it may be swabbed with a disinfectant.

FIG. 3 illustrates a first embodiment of a valve of the present invention that has been assembled using a first assembly method. The spike 24, with contiguous inner conduit 18, is affixed to the housing 12 through the association of the external portion of annular cuff 28 and the inner surface 254 of annular ring 14. Specifically, the annular cuff 28 forms a tight fit within the annular ring 14 so that the force of friction between the external portion of annular cuff 28 and the inner surface 254 of annular ring 14 secures the spike 24 inside the housing 12. This first method of assembly requires that sufficient force be applied to the distal end of the spike 24 to overcome the force of friction between the annular cuff 28 and the annular ring 14, while holding the housing 12 in place, so that the spike 24 slides toward the proximal end of the housing 12, until the rim 28a of the annular cuff 28 abuts the underside of the annular ring 14. Alternatively, the spike 24 can be held in place, while the housing 12 is forced around the outside of the spike 24. A person of skill in the art will know of numerous techniques by which this method can be accomplished. In addition, although not necessarily required, the spike 24 may be affixed to the housing 12 by any one of a variety of additional measures known to those of skill in the art including, but not limited to, heat sealing, glue, pressure lock, bonding or the like.

Proper selection of the dimensions of the annular cuff 28 and the annular ring 14 will provide a fluid tight closure for the valve 10. However, if the outside diameter of the annular cuff 28 is too small relative to the inside diameter of the annular ring 14 then, referring to FIG. 3, the spike 24 may slip in a downward direction relative to the housing 12, which may cause the valve 10 to leak. On the other hand, if the outside diameter of the annular cuff 28 is too large relative to the inside diameter of the annular ring 14, then the housing 12 may crack, particularly when the valve 10 is used to conduct lipids, or other fats, which may cause the entire spike 24 to expand. Although one of skill in the art will be able to determine appropriate dimensions for the annular cuff 28 and the annular ring 14, the present inventors have developed an improved method of assembling an improved valve 11 of the present invention which will be described below under the heading "IMPROVED METHOD AND APPARATUS FOR ASSEMBLY." This improved valve and improved method of assembly will reduce the likelihood that a valve will either leak or crack, by securing the spike 24 inside the body 12, without requiring as much pressure between the annular cuff 28 and the annular ring 14.

The seal 36 fits into the annular cuff 28 and is held in place by an internal lip 27 along the internal portion of the annular ring 14 of the housing 12. The length of the spike 24 is such that, after assembly, the tip of the spike rests below the plane defined by the lip 25 of the housing 12. Preferably, the spike tip 32 is approximately from 0.525" to 0.1" below the lip 25 of the housing 12. The seal 36 fits snugly against the spike 24 and is essentially flush with the lip 25 of the housing 12. The spike tip 32 is thus embedded within the seal cap 40 prior to use or may be approximately 0.025" distal the seal cap 40 when the valve 10 is in the closed position. The inner conduit 18 is partially shielded by the bell shaped skirt 16 of the housing 12 (see FIGS. 1–3). The inner surface 250 of the bell shaped skirt 16 preferably has protruding threads 45 as an optional locking mechanism for attaching a medical implement thereto. Further, other medical devices can be pressure fit over the outer portion of inner conduit 18 without direct association with the protruding threads 45.

During use, the invention is designed to be adapted as a two-way valve. The orientation of the valve is independent to fluid flow and dependent on the preferred orientation of the preexisting connections. Thus, the invention can be used as a valve connector for an intravenous central or peripheral piggyback connector in either orientation. Parenteral fluid is delivered to patients through tubing such that the liquid flows from a container through a needle into the patient. The containers are frequently changed or additional fluid bottles are added. The invention disclosed herein is designed to interconnect medical implements along the route of fluid delivery to the patient. However, the invention is also useful in any environment in which a resealable fluid valve is desired. During use, a connector of the appropriate size is fitted over the inner conduit 18. Locking can be achieved by a Luer-Lock mechanism, a pressure fit or any other locking mechanisms known to those with skill in the art, as described above. Thus, in one example, fluid passes from the inner conduit 18 into the spike 26. However, fluid flow is locked in place by the seal 36.

FIGS. 4 and 5 illustrate valve activation. In FIG. 4, the medical implement connecting to the proximal end of the valve 10 is a syringe 46. However, this connecting implement could be any number of medical implements known to those of skill in the art. The nose 48 of the syringe 46 is placed on the seal cap 40 inside the lip 25 of the housing 12. The application of pressure on the syringe 46 in the direction of the arrows, as illustrated in FIG. 4 creates pressure on seal cap 40. The resulting downward pressure compresses the seal 36. This pushes the tip 32 of the spike 26 through the seal cap 40 to expose the through-holes 34. Compression is facilitated by the grooves 38. Fluid is now able to flow into the syringe 46, or vice versa, depending on whether fluid is to be withdrawn from the patient or medication injected into the patient. FIG. 5 shows valve 10 opened by insertion of the nose 48 of the syringe 46 into the opening 25a. A syringe plunger 49 in the syringe 46 is retracted thereby creating a vacuum to draw fluid through the valve 10 into the syringe. For intravenous applications, the valve 10 can be orientated in the position diagramed in FIGS. 4 and 5, or it can be rotated 180° such that fluid flows in the opposite direction.

Upon removal of the syringe from spike 26, as shown in FIG. 4, the seal 36 is free to return to its original shape and cover through-holes 34. The ability of the seal 36 to return to its original shape is determined by the resiliency of the material used to prepare the seal 36. In addition, the ability of the seal 36 to return to its original shape is facilitated by the protruding ridges 30 formed on the external surface of the spike. During compression, a vacuum may form in the area between the spike 26 and the seal 36, thereby preventing the seal 36 from returning to its original position. The protruding ridges permit air to pass along the spike/seal interface to prevent vacuum formation and allow free return of the seal. The ability of the seal 36 to deform reversibly and return to its original position is particularly useful because (1) it immediately stops fluid flow through the valve 10, (2) it covers the recessed spike 26 to maintain its sterility, and (3) it reduces the risk that the spike could inadvertently pierce another object or person. In addition, since the valve 10 lacks movable parts, except for the seal, it is unlikely that when the seal 36 is pushed down, the valve 10 would fail to function.

Advantageously, the through-holes 34 are located relatively low on the spike 26. Thus, the through-holes 34 are sealed relatively early in the process as the seal 36 returns to its original configuration when the valve 10 is closed. In one preferred embodiment the through-holes 34 are located 0.075" below the spike tip 32 (see FIG. 2). Additionally, the through-holes 34 are sealed even if the seal 36 does not fully return to its original configuration depicted in FIG. 4. Further, the ability of the seal 36 to return reversibly to its original position permits the reuse of the connector valve 10. Following disconnection, and before reuse, the surface of pierced seal cap 40 is essentially flush with the housing 12. Thus, this flush surface can advantageously be sterilized with alcohol or other surface decontaminating substances. The skirt 16 and upper conduit 20 advantageously shield both connections from the surrounding environment to protect the sterility of the connection. Further, both the skirt 16 and upper conduit 20 function as collection reservoirs to prevent fluid from dripping from the valve 10 during manipulation.

A cover cap (not shown) can be supplied to fit over the upper conduit 20 as further protection for the seal surface between use. Such a cover cap, however, is not needed to maintain sterility since the seal 36 may be swabbed with a disinfectant after each use. The reversibility of the seal 36 makes the valve 10 particularly attractive as a connector valve to provide fluid communication between two fluid lines. Therefore, the present invention provides for placing a first fluid line in communication with a second fluid line using the valve disclosed herein. The reversibility of the valve 10 permits multiple fluid lines to be successively added, for example, to a fluid line in direct communication with a patient's vein. Since the valve is easily sterilizable and sealable, fluid lines can be added and removed without disconnecting venous contact.

The valve 10 is preferably prepared from a hard plastic, but it is additionally contemplated that the valve could be prepared from other medically inert materials known to those of skill in the art. The spike element 24 is preferably prepared from the same material as the housing 12. One particular advantage of this invention is that it does not rely on the use of metal needles. This dramatically reduces the risk of skin puncture during use and manufacture. Further, the upper conduit 20 serves as a shield to the spike 26 such that skin puncture is further reduced. The spike 26 need only be strong enough to penetrate the seal cap 40, or if necessary, to pierce a connecting septum.

In the embodiment of the invention illustrated in FIGS. 2-4, the through-holes 34 are placed distal spike tip 32. This placement provides two important advantages. First, the placement of the through-holes 34 facilitates resealing of the valve 10 after use. Second, if the through-holes were placed at the spike tip 32, the holes 34 may core the seal cap 40 thereby introducing seal particulate into the fluid flow and possibly plugging the holes 34. Thus, the longitudinal placement of the through-holes distal spike tip 32 prevents the introduction of particulates into the fluid path and/or plugging of the through-holes 34. It is additionally contemplated that the number and diameter of the through-holes 34 can be adjusted to accommodate different fluid velocities. In a preferred embodiment, the preferred velocity of fluid passing through the through-holes 34 is equal to or greater than the flow rate through an 18 gauge needle. Through-holes larger than 18 gauge will, of course, facilitate greater fluid velocities.

An important advantage of the invention is that the valve 10 has very little dead space, thus the volume of liquid entering into the valve is substantially equivalent to the volume of fluid leaving the valve. Further, the total equivalent fluid volume of the valve is very small such that the volume of fluid flowing through the system in order to place the valve in fluid communication with a medical implement such as a syringe 46 is substantially zero.

Alternate Embodiments

Figure 6:
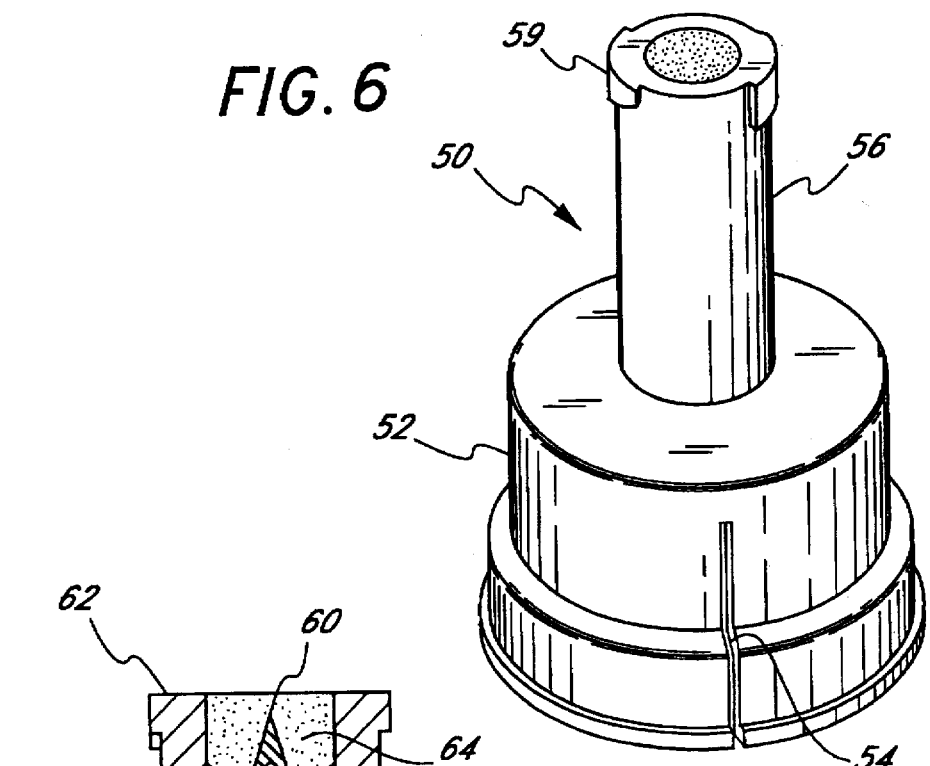
FIG. 6 is a perspective view of a second embodiment of the invention.

In another preferred embodiment of the invention, illustrated by FIGS. 6 and 7, a disposable sterile adaptor valve 50 is provided to function as a resealable lid for a container (not shown) of fluid. The fluid can thus be removed from the fluid container or permitted to flow from the container into a medical implement adapted to house fluid in a sterile manner. As is the conventional practice, an open mouth of the container will ordinarily be sealed with a cover member (not shown).

FIG. 6 shows an adaptor valve 50 having a body including an adaptor skirt 52. The adaptor skirt 52 will preferably fit snugly over the open mouth of the container. The skirt 52 may be of any size to accommodate a range of container sizes. A lengthwise slit 54 is preferably provided in at least one location along the length of the skirt to ensure a snug fit between the skirt 52 and the container. A chamber 56, preferably tubular in configuration, extends upward from the skirt 52 and is similar in construction and design to the upper chamber 20 of the first preferred embodiment. Similar to the first embodiment, the proximal portion of the valve contains a locking mechanism 59 that preferably comprises a Luer-Lock device or other locking device known to those of skill in the art.

As depicted in FIG. 7 a spike 58 extends upward through a tubular chamber 56. A spike tip 60 is preferably recessed from a proximal lip 62 of the tubular chamber 56. In a closed position, this tip 60 is covered by a seal 64, which is essentially the same as seal 36. Protruding ridges 66 and seal grooves 68 facilitate seal compression in the open position and promote closure following use. Thus, in the closed position as illustrated in FIG. 7, the seal 64 covers the through-holes 70 to prevent fluid out-flow from the container. The adaptor valve 50 contains a second spike 72 which points in the opposite direction as spike 58. These spikes 52 and 72 are in fluid communication with each other. The spike 72 extends downward inside the adapter skirt 52. The two spikes preferably form one component of the valve 50 while the skirt 52 and upper chamber form a second component. These two components can be assembled in a manner like that of the valve 10. The spike 72, like the spike 58, has longitudinal through-holes 74 and a tip 76. The through-holes 74 are located inward of the tip 76. The adaptor valve 50 is thus useable with containers holding sterile medicament having a cover or septum seal at the open mouth of the container. Examples of containers with such seals contemplated for use with this invention include dosage bottles for intramuscular injector antibiotic containers or the like. However, it is also contemplated that the valve 50 can be adapted with its own seal and locking mechanism to permit the valve to be employed on a variety of containers for medicaments or other fluids. Medicaments in these types of containers are preferably maintained under sterile conditions and the volume and nature of the medicament is such that multiple aliquots are intermittently removed over time. If the medicament is reconstituted, then, during use, any covering over the opening on the container is removed to reveal the rubber septum. The adaptor valve 50 is placed over the septum and direct pressure is applied to pierce distal spike 72 through the septum and into the container. A syringe or the like can then be applied, as depicted in FIG. 4, in association with the first preferred embodiment, to withdraw fluid from the container. The pressure of the nose 48 over the spike 58 pushes spike tip 60 through seal 64. At the same time, the seal 64 is pushed back and compresses. Compression is accommodated by seal grooves 68. Fluid is withdrawn from the container and the syringe is removed from the spike 58. Release of the pressure applied to the seal 64 permits the seal to return to its original configuration. The spike ridges 66 facilitate seal reversibility.

Often the ingredients housed in containers are those that can be lyophilized at purchase. Lyophilized ingredients require reconstitution before use. If the medicament requires reconstitution before use, then sterile water, saline, or other fluid can be introduced into the container before fluid is extracted. The two-way nature of the valve permits this without any special adaptation. After the syringe is removed, the adaptor valve 50 automatically seals. Subsequently, aliquots can be removed from the container by syringe or the like. Alcohol or other compatible surface sterilizing agent can be used to wipe the lip 62 and seal 64 before each use. Similar to the first embodiment, it is additionally contemplated that a cap can be provided to fit over upper chamber lip 62 between use.

The adaptor valve 50 can be adapted to function as a medicament adaptor for an intravenous container. In this case, the adaptor valve 50 is placed on a medicament container for intravenous delivery and attached via tubing to an intravenous feed. Thus, the adaptor valve 50 can be placed in fluid communication with a connector valve of FIG. 1 to facilitate the flow of medicament from intravenous drip bottles.

Figure 9:
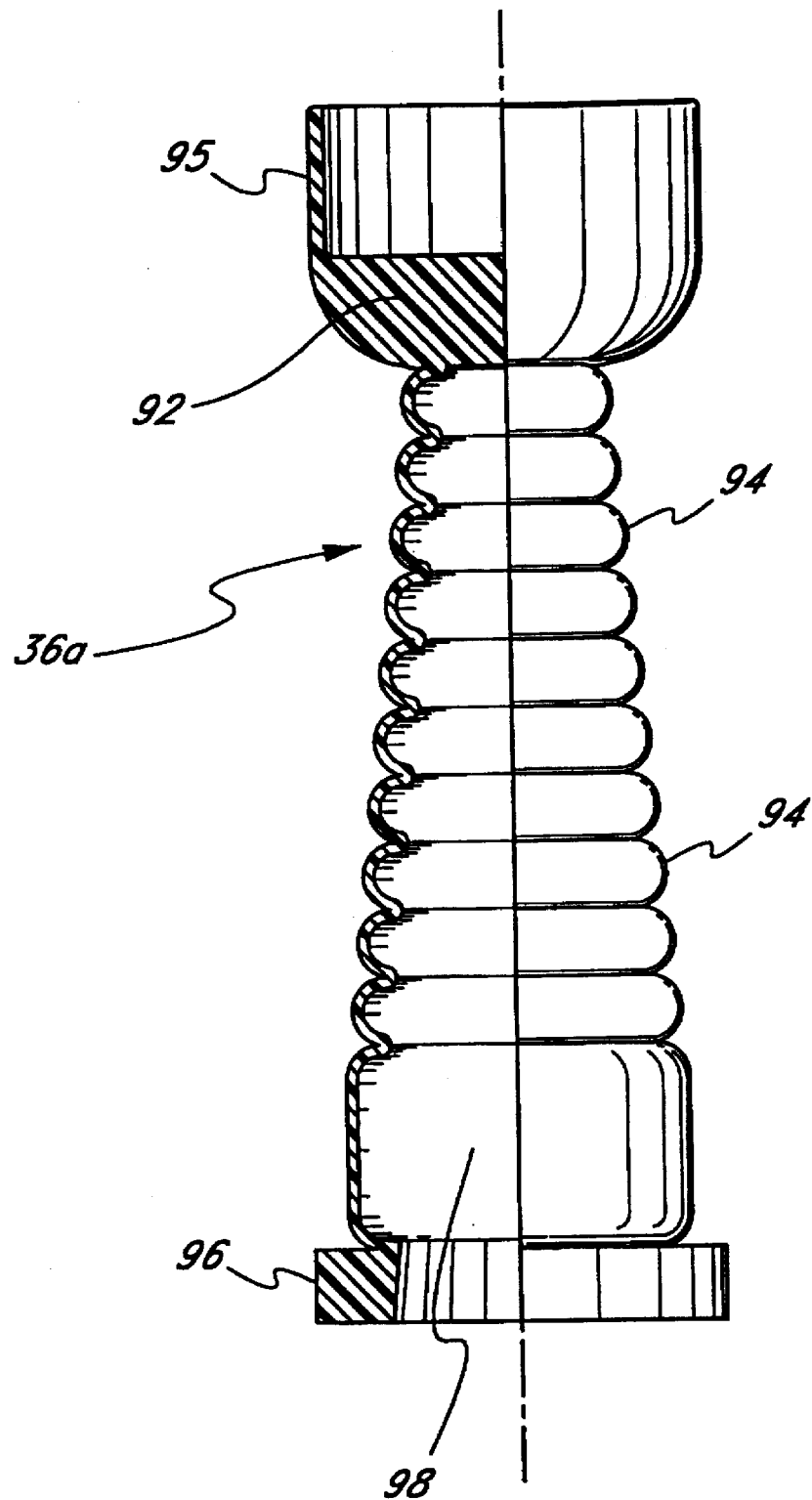
FIG. 9 is a side elevation view, partially in cross-section, of a third embodiment of the seal.

An alternative embodiment of the seal, a seal 36a, is shown in FIG. 9. Seal 36a comprises a seal cap 92 at the proximal end thereof and a seal lip 96 at the distal end thereof. A cup-like annular flange 95 is provided proximal seal cap 92. The seal cap 92 and seal lip 96 are connected by a seal wall consisting of a plurality of ringed wall portions 94 that expand and collapse in an accordion like fashion. During compression of the seal 36a, the diameter of the ringed wall portions 94 expand outward in the radial direction. There are air pockets 13a (FIG. 10) between ring portions 94 and the housing and air pockets 13b between spike 24 and seal 36a. The seal 36a contains a cavity 98 distal seal cap 92 and adjacent the ringed wall portions 94. The seal 36a interacts with spike 26 (FIG. 2) and other components of the present invention in a similar fashion to seal 36 of FIG. 2.

Figure 10:
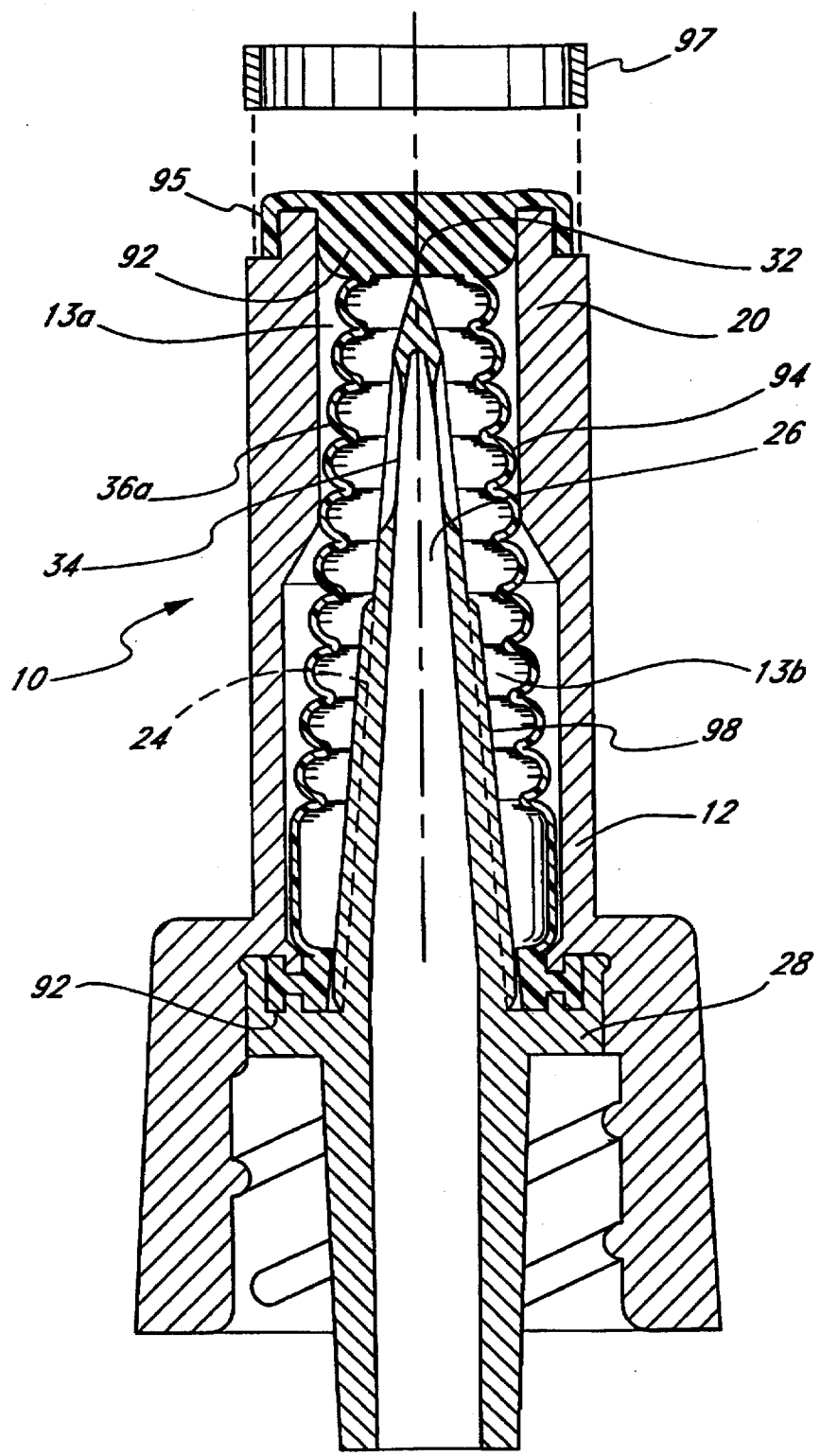
FIG. 10 is a longitudinal cross-sectional view of the assembled valve of FIG. 1 using the seal of FIG. 9.

Referring to FIG. 10, the cup-like annular flange 95 may be stretched around the upper conduit 20 and held in place by an annular ring 97. This creates a trampoline like effect that assists returning the seal 36a to a decompressed state after withdrawal of a syringe (not shown). This embodiment has two advantages. First, the proximal end of the valve 10 can be swabbed with alcohol or other disinfectant without leakage of disinfectant into the valve 10. Second, by affixing cup-like annular flange 95 to upper conduit 20 at the proximal end thereof with annular ring 97, the repeated deformation and reformation of the seal 36a is assisted.

Figure 11:
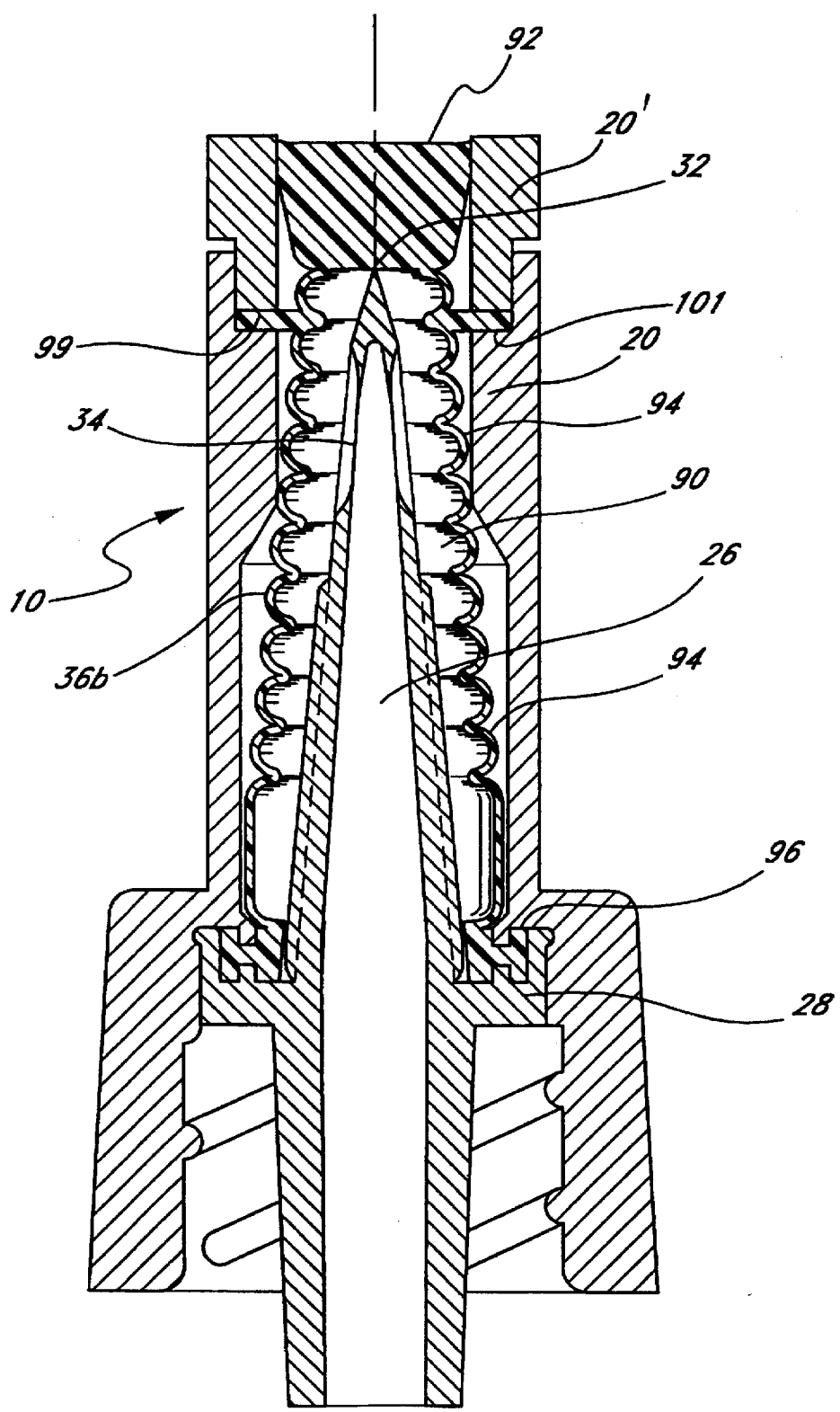
FIG. 11 is a longitudinal cross-sectional view of the assembled valve of FIG. 1 using a fourth embodiment of the seal.

An alternative embodiment of the seal, a seal 36b is shown in connection with the valve 10 in FIG. 11. The seal 36b is similar to the seal 36a and is comprised of seal cap 92, a side wall consisting of ringed wall portions 94 and a seal lip 96. It also has an outwardly extending ring 99 which is at a right angle with respect to the longitudinal axis of the valve 10. This ring 99 is used to attach the seal 36b to upper conduit 20. Preferably, an upper conduit annular plug 20' is inserted within upper conduit 20 to create a tight fit between perpendicular ring 99, a ledge 101 in the upper conduit 20, and the plug 20'. The ring 99 assists in the reformation of seal 36b to enclose spike 26 upon withdrawal of a syringe (not shown).

Figure 12:
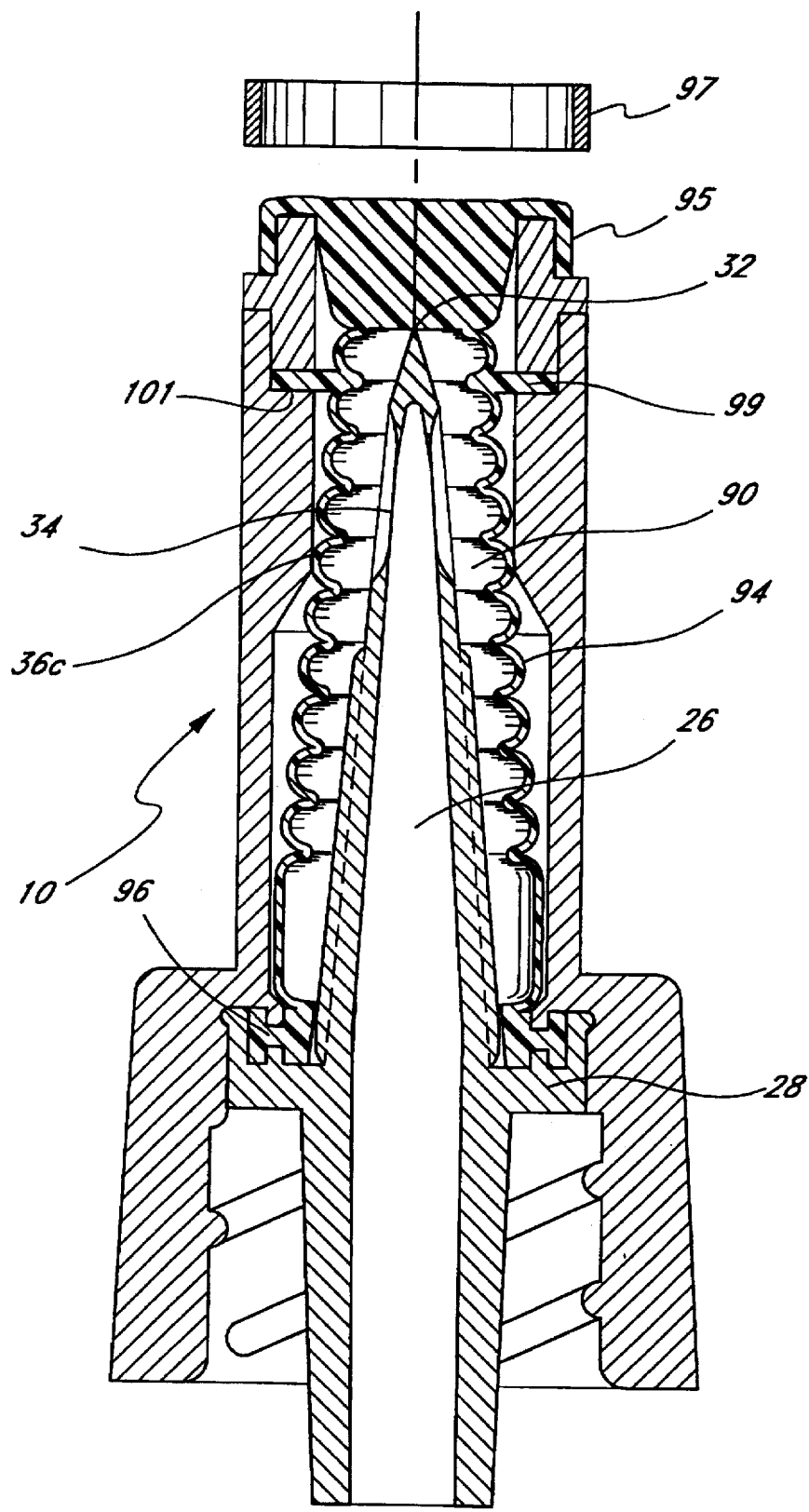
FIG. 12 is a longitudinal cross-sectional view of the assembled valve of FIG. 1 using a fifth embodiment of the seal.

As shown in FIG. 12, the cup-like annular flange 95 and ring 99 may both be used in connection with the valve 10, to provide the seal 36c. This seal 36c, provides rapid reformation upon withdrawal of a syringe (not shown) and realizes the advantages of both the seals 36a and 36b.

Another alternative embodiment of the seal, a seal 36d, is shown in FIG. 13. In this embodiment, the seal 36d is comprised of seal cap 92, seal lip 96, and a side wall 150 comprised of circular tires 100 stacked in series one on top of an adjacent larger diameter lower tire. The circular tires 100 are preferably solid throughout the diameter of the cross-section thereof. These circular tires 100 will deform and reform upon, respectively, compression and decompression of the seal 36d, thereby exposing or covering a spike (not shown) as the case may be.

Figure 14:
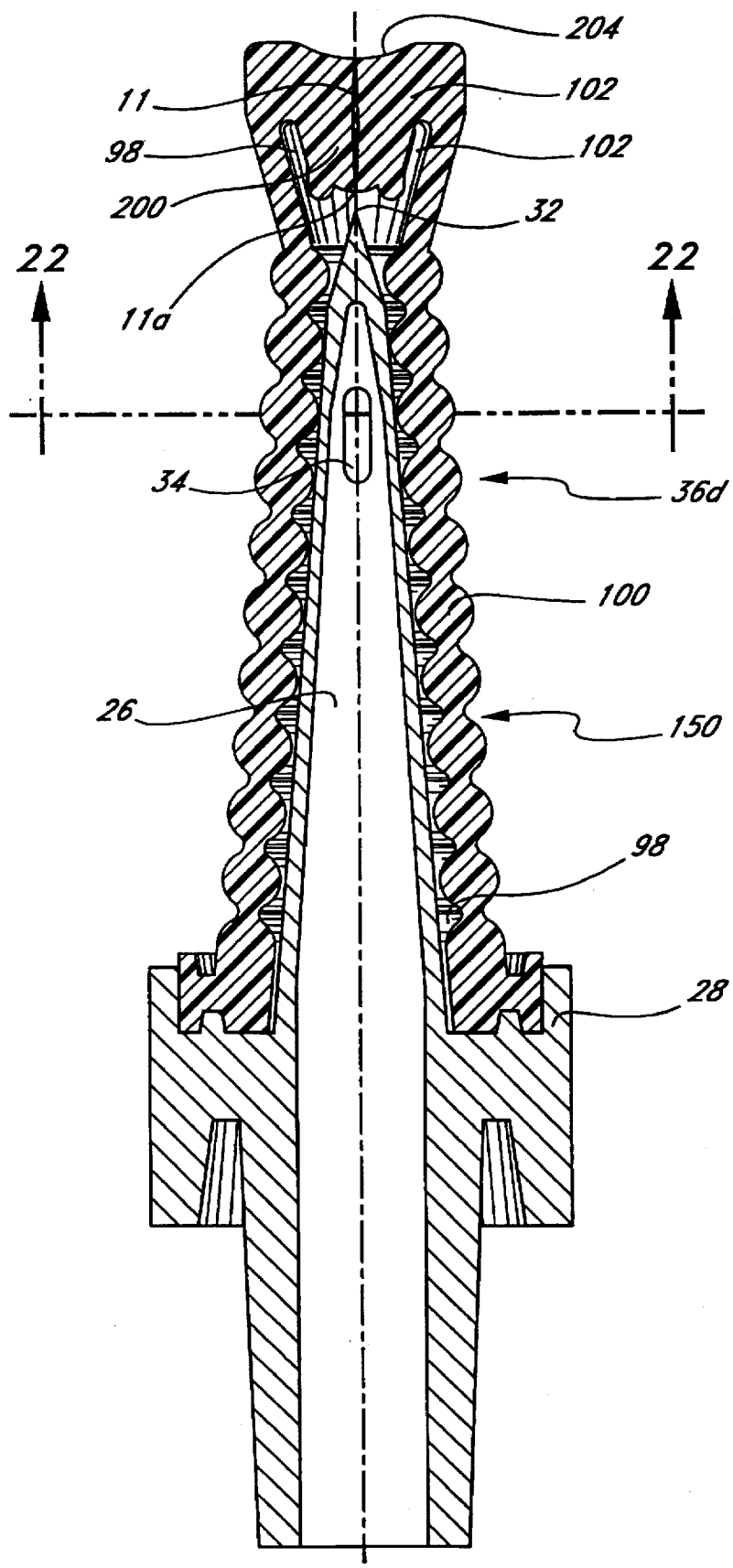
FIG. 14 is a longitudinal section of the seal shown in FIG. 13 used in connection with the spike device shown in FIG. 2.
Figure 15:
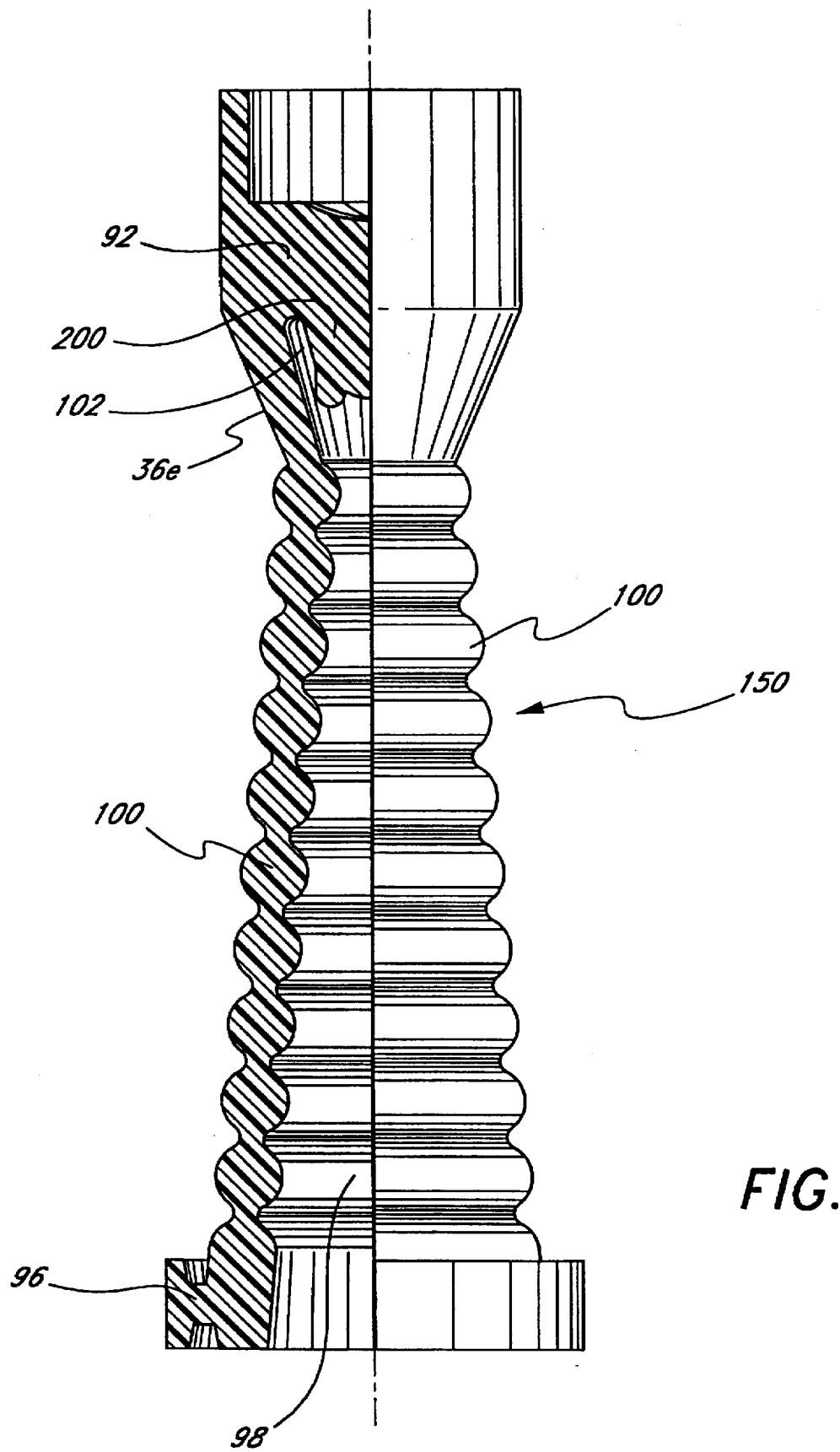
FIG. 15 is a longitudinal partial cross-sectional view of a seventh embodiment of the seal of this invention.
Figure 16:
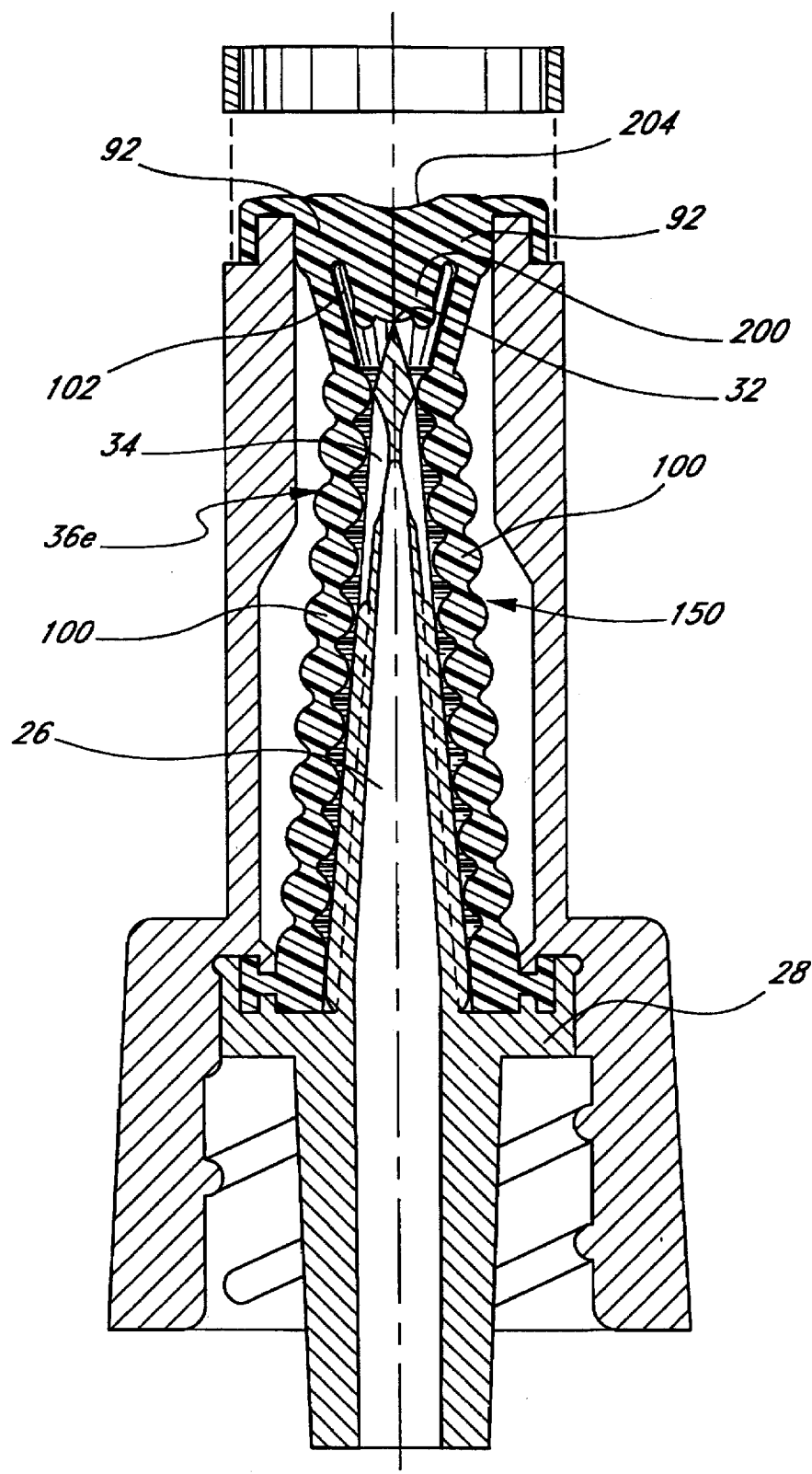
FIG. 16 is a longitudinal cross-sectional view, after assembly, of the embodiment of the valve shown utilizing the seal of FIG. 15.
Figure 17:
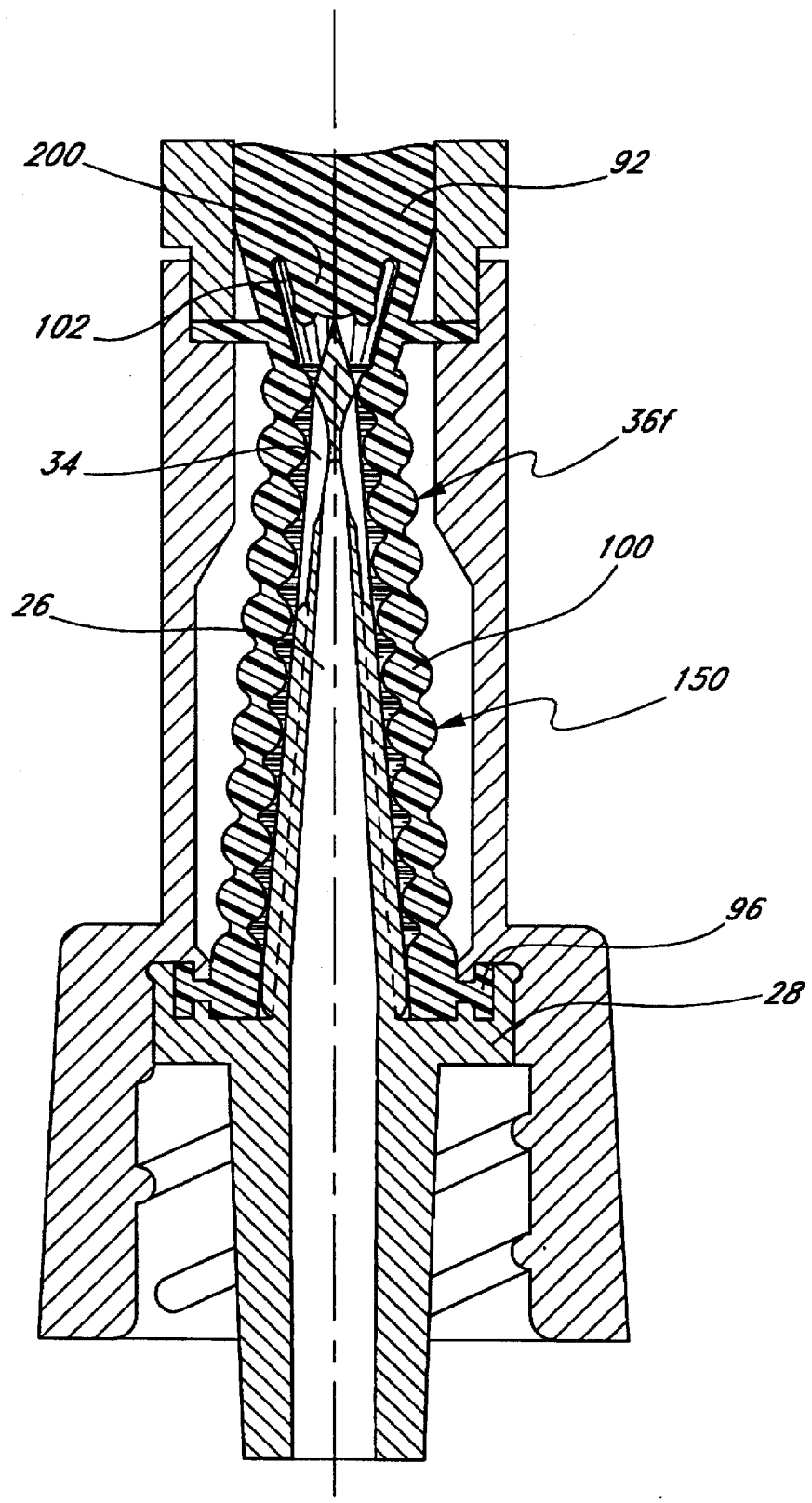
FIG. 17 is a longitudinal cross-sectional view, after assembly, of the eighth embodiment of the valve of this invention.
Figure 18:
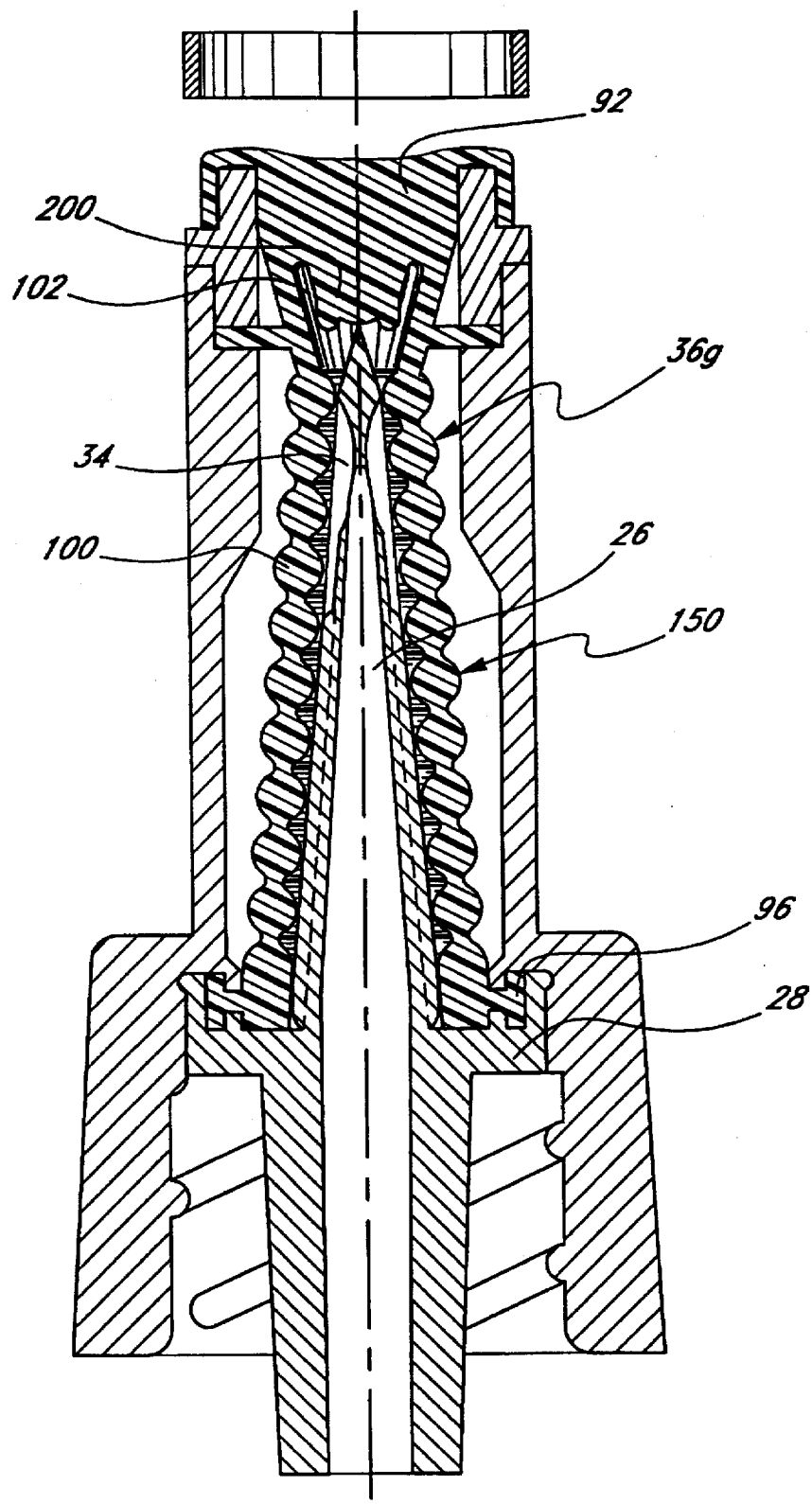
FIG. 18 is a longitudinal cross-sectional view, after assembly, of the ninth embodiment of the valve of this invention.
Figure 19:
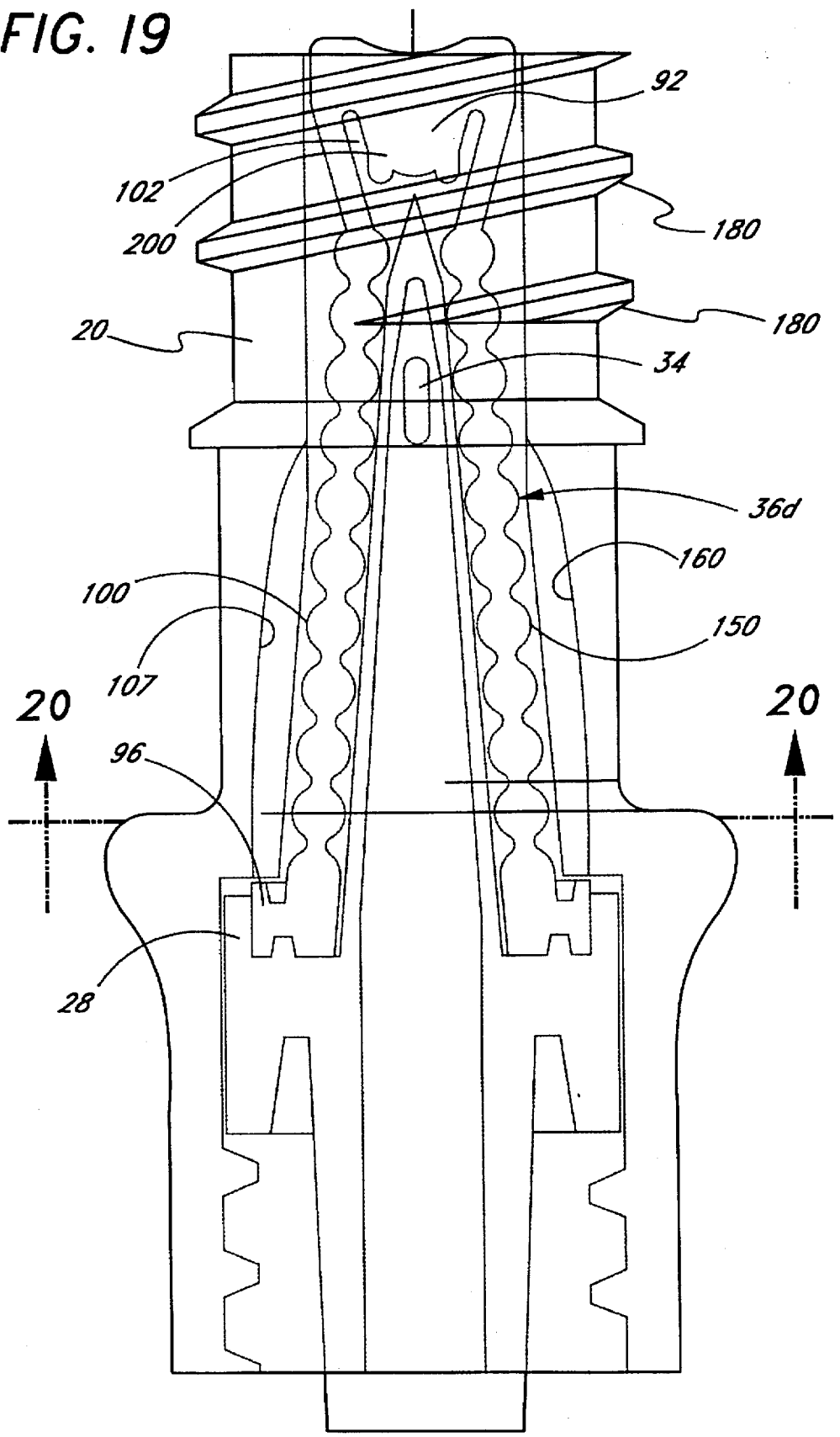
FIG. 19 is a side elevation view, after assembly, of the seal and spike shown in FIG. 14 connected to the body or housing shown in FIGS. 20 and 21.
Figure 20:
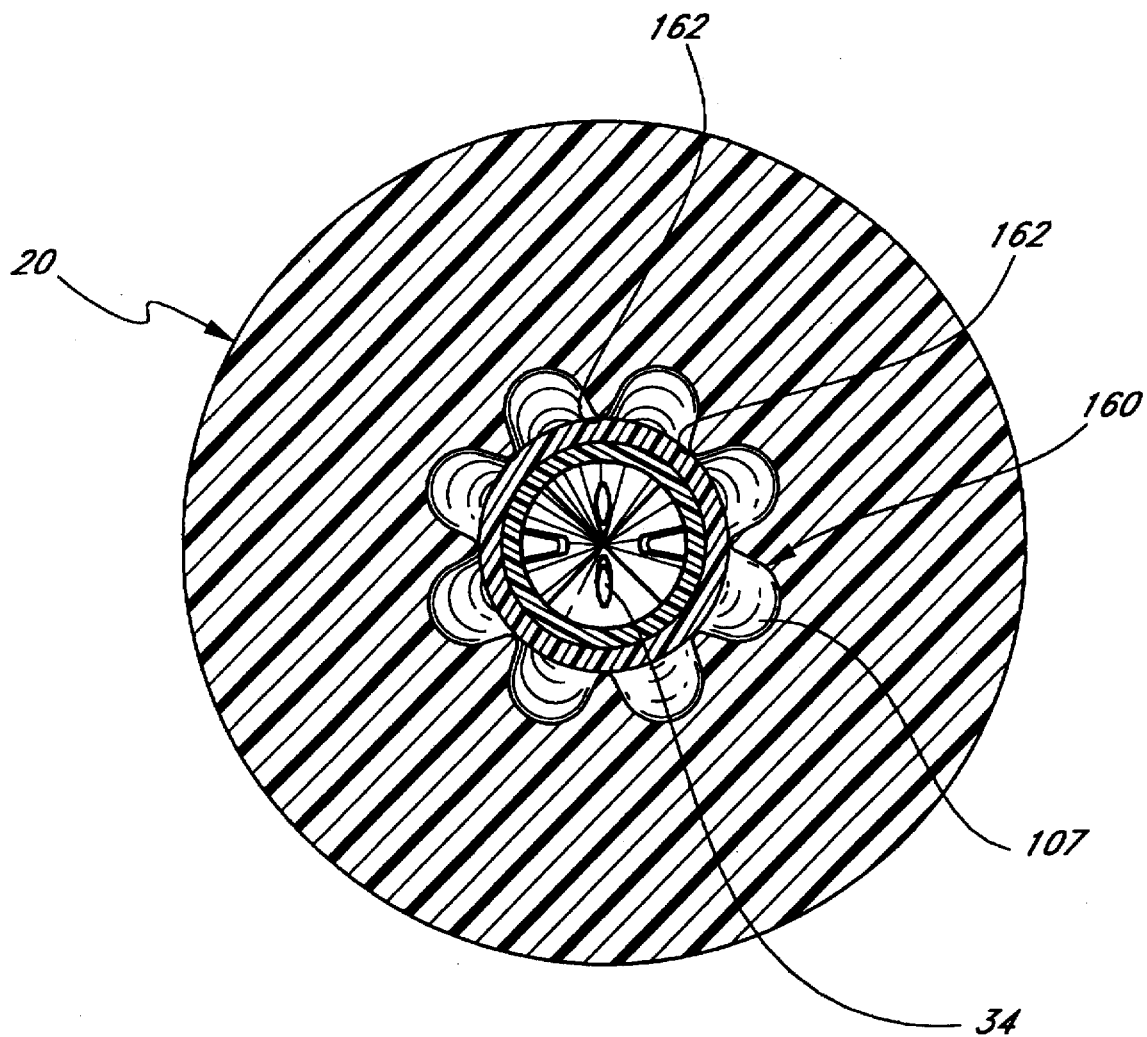
FIG. 20 is a cross-sectional view taken along line 20—20 of FIG. 19.
Figure 21:
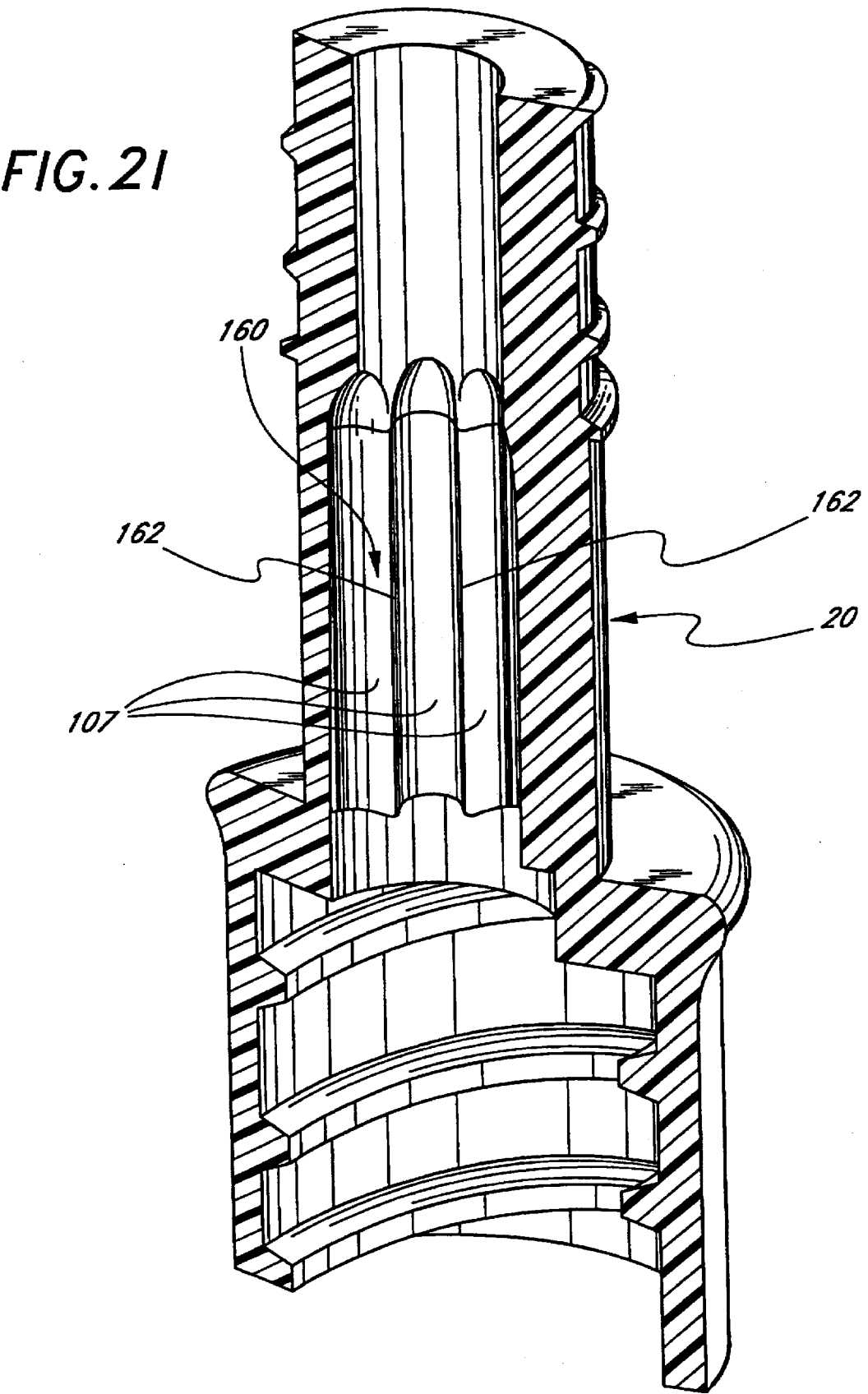
FIG. 21 is a perspective view, with sections broken away to show the wall structure of the cavity containing the seal shown in FIGS. 13 and 14.

As mentioned above, preferably the seal 36d has a precut slit 11 in the cap 92 lying along the longitudinal axis of the valve 10. The seal cap 92 has a unique configuration that insures that the slit 11 closes and is sealed upon withdrawal of a syringe (not shown) and reformation of the seal 36d. It includes an enlarged, internal, pressure responsive member 200 which is integral with the cap 92. Between the proximal end of the side wall 150 and the member 200 is an annular space 102 which is filled with the fluid in the cavity 98. This fluid is under pressure, for example at the blood pressure of the patient to which the valve 10 is attached. Referring to FIG. 14, fluid, for example the patient's blood, flows through the holes 34 in the spike 26, filling the cavity 102. This fluid presses against the exterior of the member 200, closing the slit 11 when the seal is decompressed as shown in FIGS. 14 and 19. The pressure from this fluid creates a high pressure seal which prevents fluid from escaping valve 10 through the slit 11. There is a semi-cylindrical annular flange tear ring 104 on the end of the member 200 which advantageously extends the useful life of seal 36d.

Preferably, there is a tear ring 104 integral with the member 200 along the perimeter of the internal surface of the member 200, and a slight saucer-like depression 204 in the external surface of the seal. The pressure responsive element in the decompressed state closes any orifice in the seal 36d to provide an essentially fluid-tight seal while in the decompressed state. The pressure responsive member 200 enables the valve to maintain a fluid-tight seal even at very high pressures sometimes experienced in medical applications, particularly when the valve 10 is connected to a patient's artery. The center of the member 200 and the annular space 102 are coaxial with the entryway 11a to the orifice 11. The pressurized fluid fills the annular space 102 to apply pressure that compresses the member 200 to tightly close the entryway to the orifice. In a preferred embodiment the distance from the entryway 11a to the proximal end of seal cap 92 is from 0.500 to 0.075 inches and more preferably approximately 0.100 inch.

Figure 22:
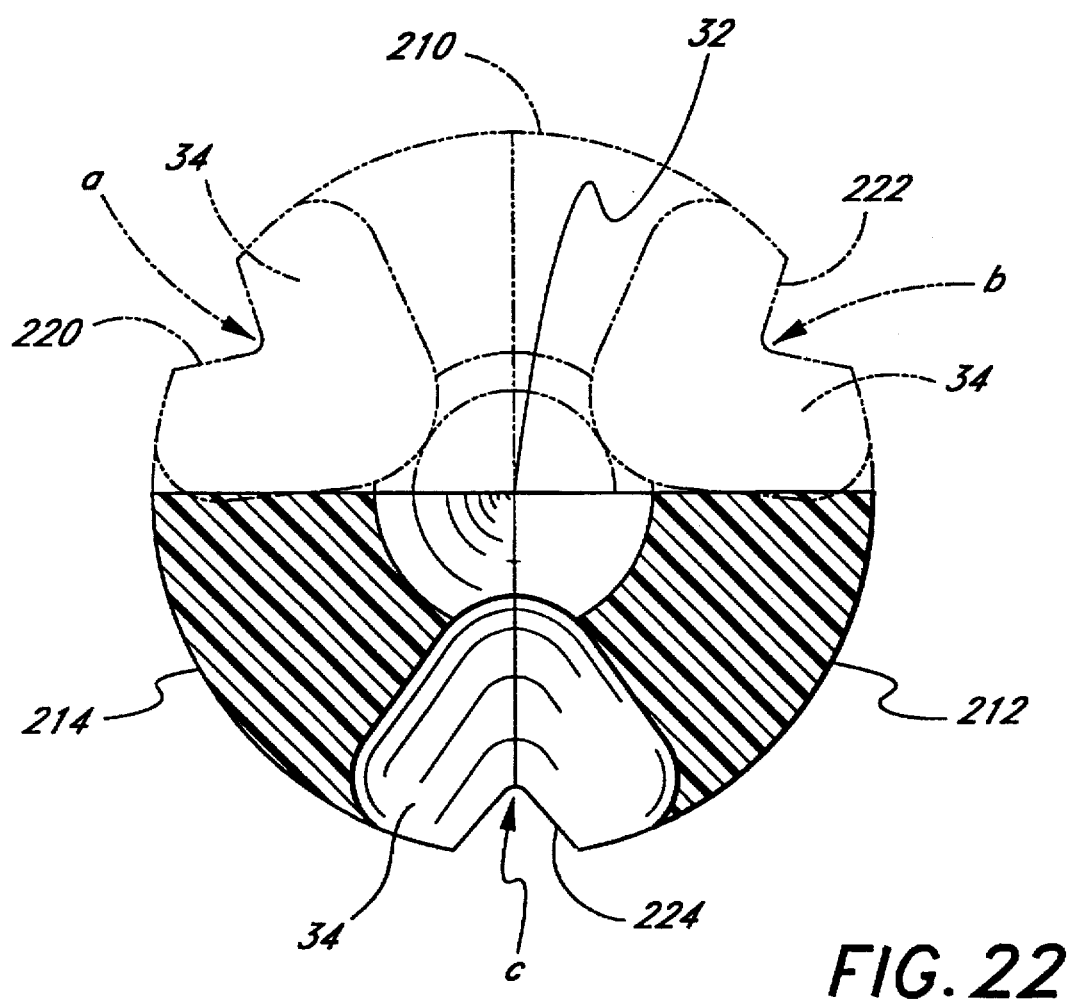
FIG. 22 is a greatly enlarged, cross-sectional view taken along line 22—22 of FIG. 14.

As best illustrated in FIG. 22, the tip 32 is designed to avoid tearing the seal. Tip 32 has three facets 210, 212, and 214 which are joined with each other along parting lines a, b, and c. This junction of the facets 210, 212, and 214 frequently is ragged and will tear the seal 36d. This is prevented by the parting lines a, b, and c, or junctions, being disposed within recesses 220, 222, and 224, respectively, to provide "buried parting lines."

Another alternative embodiment of the present invention using the seal 36d is shown in FIG. 8 and FIGS. 19 through 21. In this embodiment, the inner wall 160 of the upper end of the conduit 20 is provided with at least one, and preferably, a plurality of radial indentations 107. The indentations 107 are disposed generally parallel to the longitudinal axis of the valve 10 in a symmetrical, star-like configuration. Each indentation has opposed lateral edges 162 which engage the seal 36d upon compression of the seal 36d. The indentations provide space into which the seal 36d expands upon compression.

Figure 8:
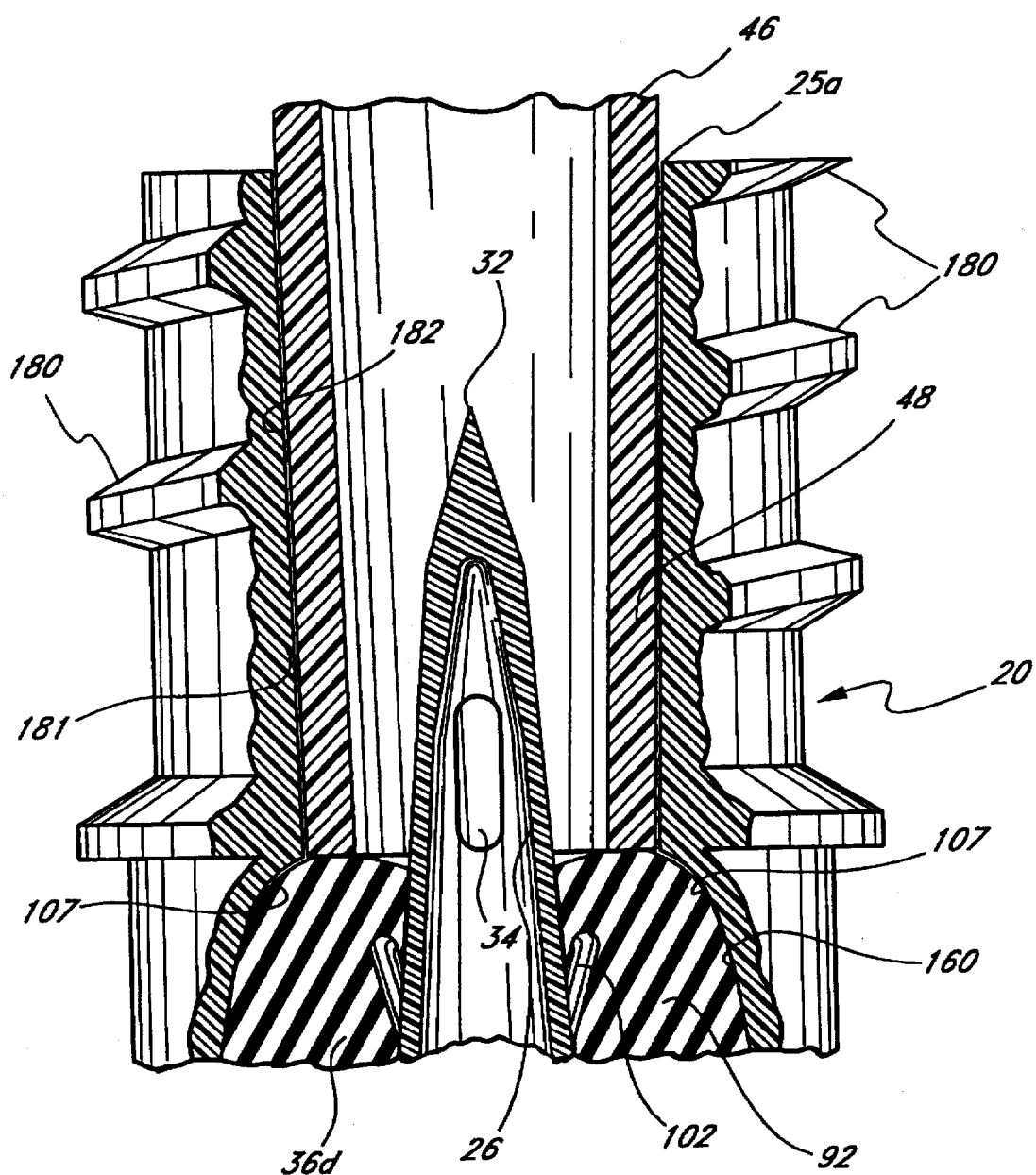
FIG. 8 is a schematic illustration of an ANSI delivery end of a medical implement compressing the seal of the valve of this invention.

As best shown in FIG. 8, the wall 181 of the proximal end of the conduit 20 is tapered inward at the same angle as the nose 48 of the syringe 46. In accordance with ANSI standards, the taper is 0.006 inch per linear inch. The wall 182 of the syringe nose 48 bears against the wall 181 as the nose slides into the opening 25a to push the seal 36d inward compressing it and forcing the tip 32 of the spike 36 to enter the slit 11. The seal 36d expands upon compression to fill essentially completely the upper portions of the indentations 107. Some sections of the seal 36d are wedged between the edges 162 and other sections fill the indentations 107. As the liquid flows through the nose 48 through-holes 34, air in the nose 48 is forced out of the nose 48 and expelled from valve 10 between the walls 181 and 182. Thus, essentially the entire prescribed dosage is delivered through the valve 10 to the patient. Fluid flows through the through-holes 34, but does not leak between either the seal 36d and the wall 181 or between the abutting walls 181 and 182.

FIGS. 15, 16, 17, and 18 depict embodiments of seals, namely, seal 36e, seal 36f, and seal 36g, which are substantially the same as the seals 36a (FIG. 10), seal 36b (FIG. 11), and seal 36c (FIG. 12), except the side wall 150 employing the circular tires 100 is used in place of the accordion wall portion 94.

Other components of the present invention interact with the various embodiments of the seal in a similar fashion to their interaction with the seal 36 of FIG. 2. Prior to use of the valve 10, it is preferable that the seal caps 40 or 92 be pierced centrally by a steel needle in the axial direction, precutting the seal to provide the slit 11 in order to allow for more rapid decompression and reformation of the seal upon piercing by the spike 26. The seals are advantageously formed from a material which can repeatedly reseal and prevent fluid from flowing around the seal material. The seal 36 should also be capable of being forced down and then spring back into position to reseal the valve. Material that is too soft will reseal effectively; however, will not be capable of springing back after opening of the valve. Material that is too hard will provide sufficient spring force; however, will not effectively seal. Thus, in a preferred embodiment, the seal is formed from a silicone having a hardness in the range from 30–70 Shore durometer units, and more preferably in the range 40–50 Shore durometer units. A cure silicone polymer in the preferred hardness range is available from Wacker Silicone Corp. of Adrian, Mich. In some embodiments of the invention, it is desirable to provide additional lubricity to the seal 36 to allow it to spring back and reseal more effectively. Dow Chemical Co. produces a silicone formulation with silicone oil built in to provide this additional lubricity.

In general, the closing of the valve 10 is provided not by the side wall of the seal 36 which immediately covers the through-holes 34, but by the seal cap 40, or seal cap 92 filling the proximal end of the cavity 98 and the opening 25a. Thus, the seal caps 40 and 92 are sufficiently thick to reseal the opening 25a effectively after valve closure. However, the seal caps 40 and 92 should also be sufficiently thin to allow them to readily return to the closed position. Preferably the thickness of the caps 40 and 92 ranges between 0.075 and 0.500 inch and more preferably may be approximately 0.100 inch.

The valve disclosed in this invention can be provided in a sterile and disposable form such that after its use in a given installation is exhausted, the device is discarded. However, as described above, in any given installation, the device can be reused multiple times. Since the device does not employ needles, there is little chance that the device will inadvertently cause skin puncture. Therefore, the extra precautions required for handling and disposing of needles is obviated. It will be apparent from the detailed description provided herein that the present invention can provide for the elimination of nearly all needles used in the medical environment. With the use of the valve of the present invention, the need for all needles except those that are directly input into a patient is, advantageously, eliminated.

Improved Medical Valve

Figure 23:
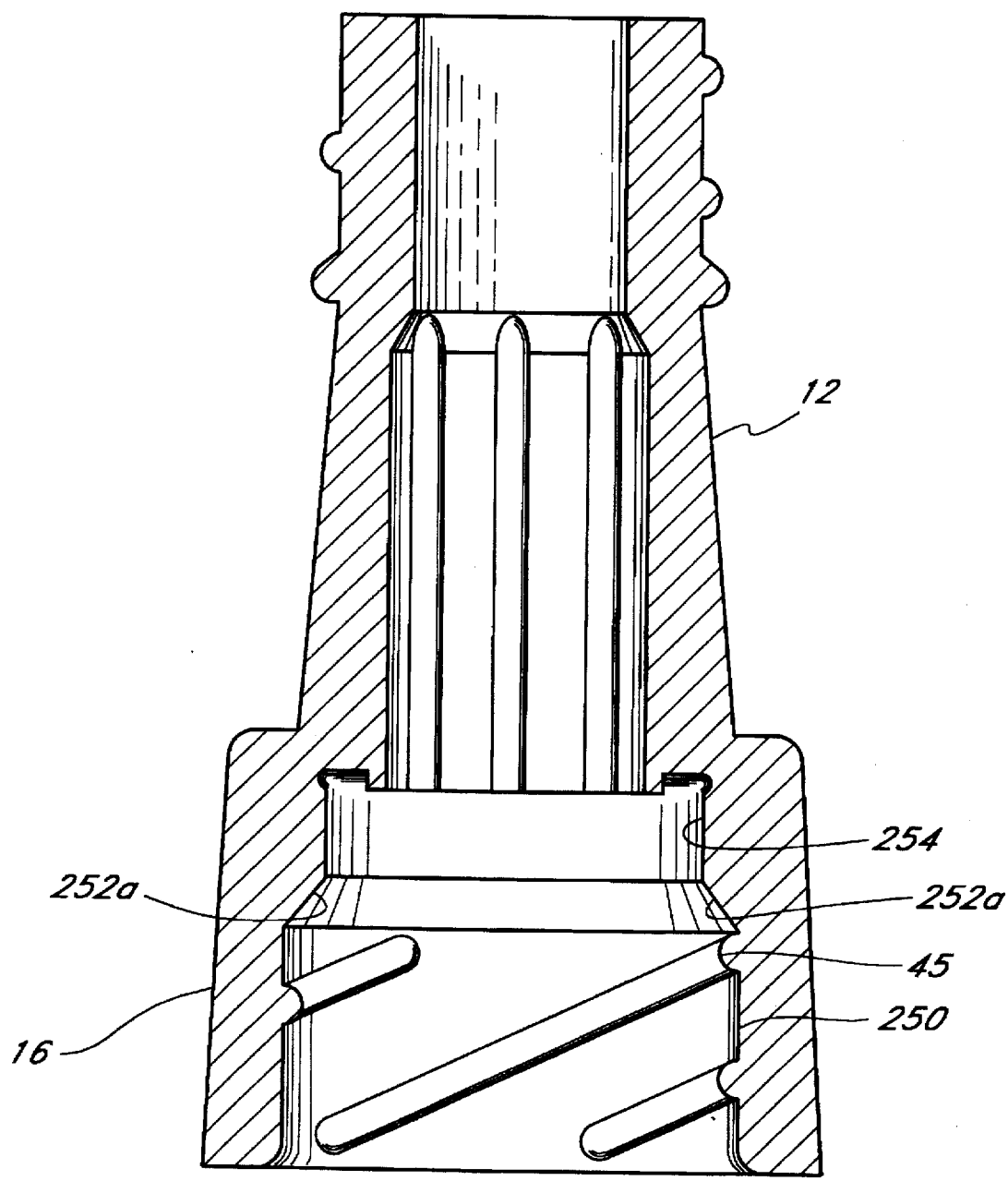
FIG. 23 is a longitudinal cross-sectional view of the body of a tenth embodiment of the valve of this invention, which is suitable for use in a second assembly method.
Figure 24:
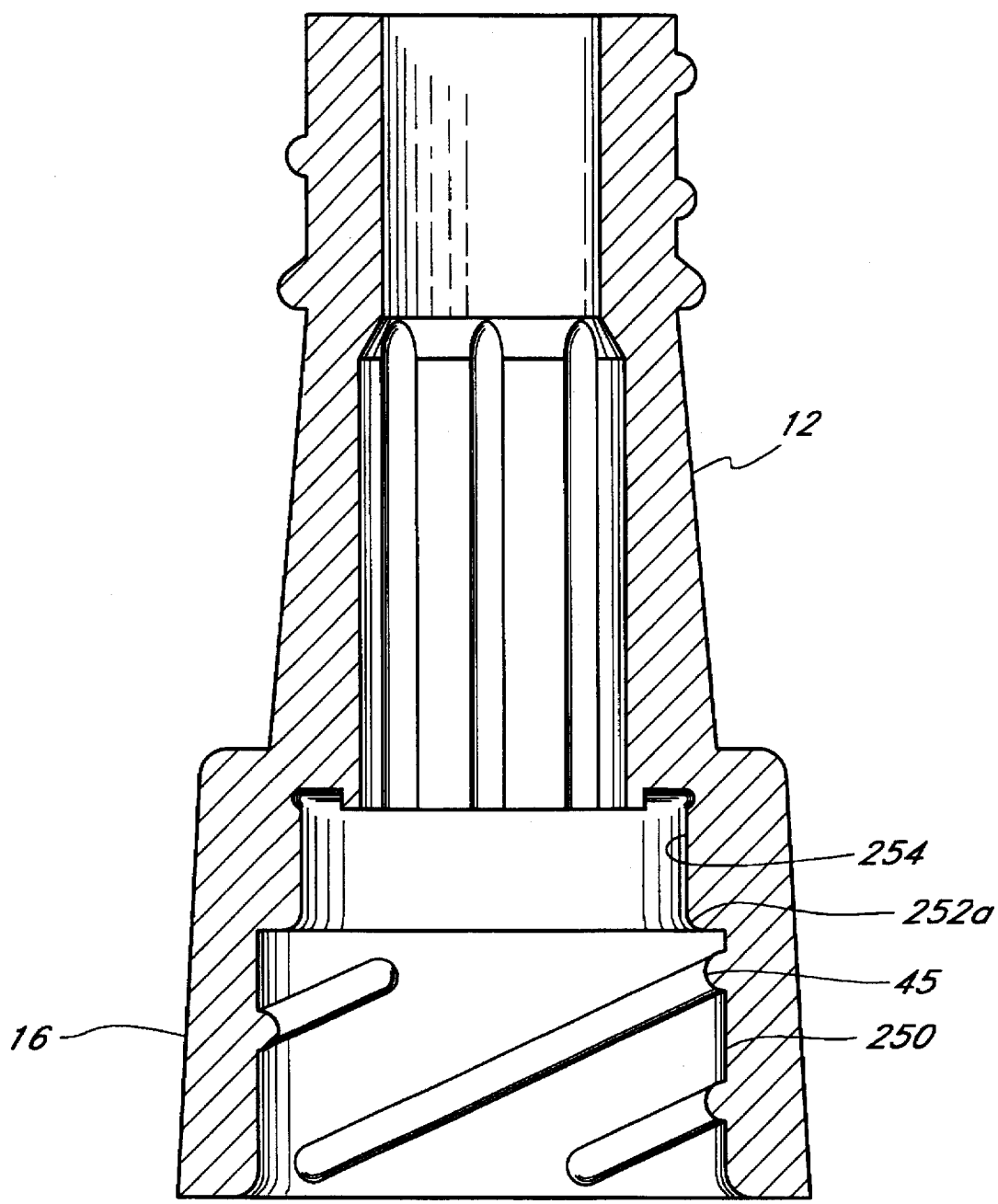
FIG. 24 is a longitudinal cross-sectional view of the body of an eleventh embodiment of the valve of this invention, which is also suitable for use in the second assembly method.

FIG. 23 illustrates a body or housing 12 of a tenth embodiment of the present invention, while FIG. 24 illustrates a body or housing 12 of an eleventh embodiment of the present invention. The housing 12 of FIG. 23 or FIG. 24 is substantially similar to housing 12 described above in conjunction with FIG. 1. Thus, the housing 12 has a bell-shaped skirt 16, an inner surface 254, protruding threads 45, an inner surface 250, and further includes a gouging surface 252a. In FIG. 24 the gouging surface 252a is illustrated as a ledge extending arcuately from the inner surface 250, while in FIG. 23 the gouging surface 252a is illustrated as a ledge extending at a slope from the inner surface 250. The housing 12 is specially designed for use with a second, and improved, method of assembly, described in more detail below. In particular, for the improved method of assembly described below, a portion of the gouging surface 252a preferably has a smaller diameter than the effective diameter of the protruding threads 45. As recognized by a person of skill in the art, other embodiments of the housing 12, with variations to the gouging surface 252a, can be used with the improved method of assembly, or a functionally equivalent method, to provide an improved medical valve 11, based on the following description of the improved valve and method.

Figure 25:
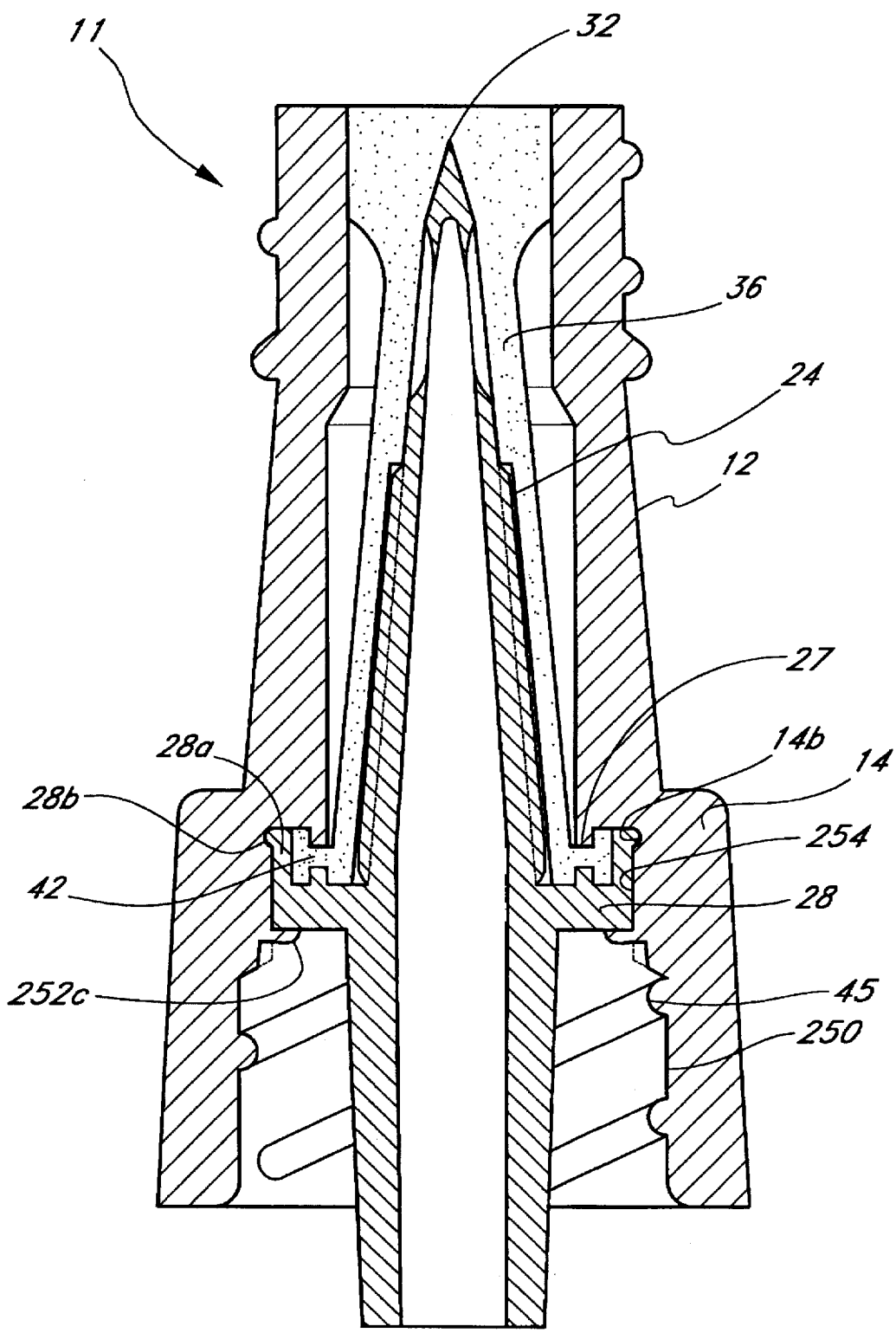
FIG. 25 is a longitudinal cross-sectional view of the tenth embodiment of the valve of the present invention, comprising the spike and seal components from FIG. 3 and the body component from FIG. 23, assembled by using the second assembly method, or a functionally equivalent method.

FIG. 25 illustrates the improved medical valve 11 comprising the housing 12 of FIG. 23 (although the valve 11 could be made with the housing 12 of FIG. 24 equally well), the spike element 24 of FIG. 3, and the seal 36 of FIG. 3. An improved medical valve 11 can also be created from the spike element 24 and seal 36 of any of the first nine embodiments. Thus, for example, an improved medical valve 11 can be assembled using the housing 12 of FIG. 23, the spike element 24 of FIG. 14, and the seal 36d of any of FIGS. 1–5, 7 and 9–19 to create a new, and preferred, embodiment. The improved medical valve 11 is essentially similar to medical valve 10, described above, with the addition of retaining tabs 252c for securing the spike element 24 and the seal 36 inside the housing 12, and a variation in the interference fit between the spike element 24 and the housing 12.

Still referring to FIG. 25, the improved medical valve 11 comprises a spike element 24 and a seal 36 mounted in the housing 12. The seal lip 42 the materials and the manufacturing process of these components, reducing manufacturing costs.

Improved Method and Apparatus for Assembly

Figure 26:
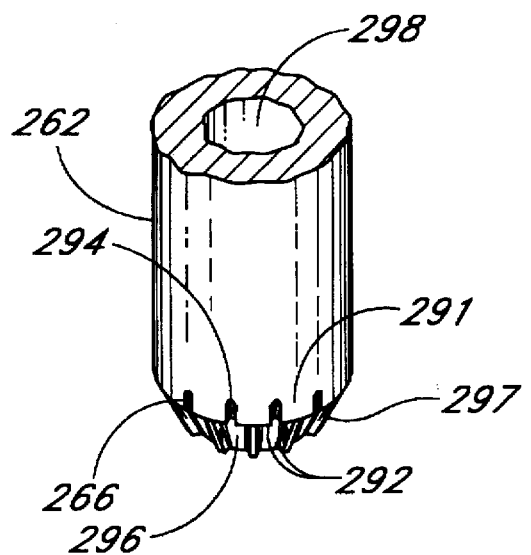
FIG. 26 is a perspective view of a gouging bit and a base which are preferably used in the second assembly method.
Figure 26:
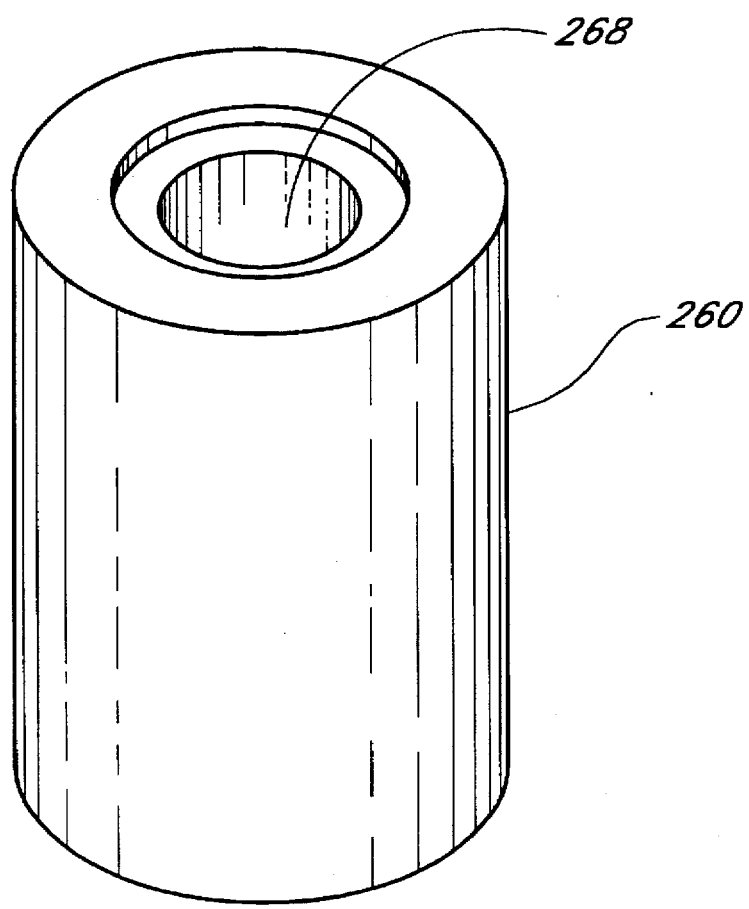
Figure 27:
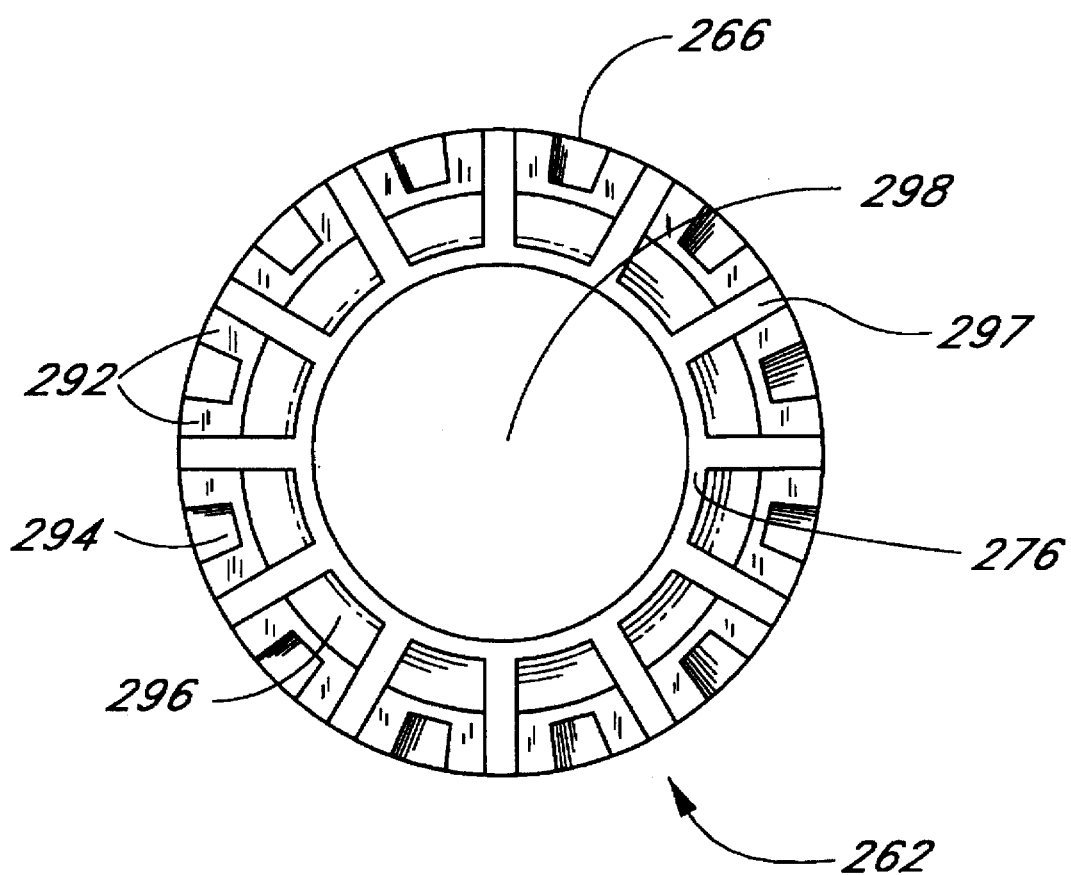
FIG. 27 is a bottom plan view of the gouging bit of FIG. 26.

FIG. 26 shows a gouging bit 262 and a base 260 that are preferably used in an improved method of assembling valve 11. The gouging bit 262 has a central bore 298 therethrough, a gouging edge 266 thereon, several guiding surfaces 292, 294, and 296, and a number of ribs 297. The base 260 includes a hole 268. FIG. 27 shows a bottom plan view of the gouging bit 262. This figure shows the several guiding surfaces 292, 294, and 296, the ribs 297, along with the bore 298 and a contact surface 276 to which the ribs 297 are connected.

Figure 28:
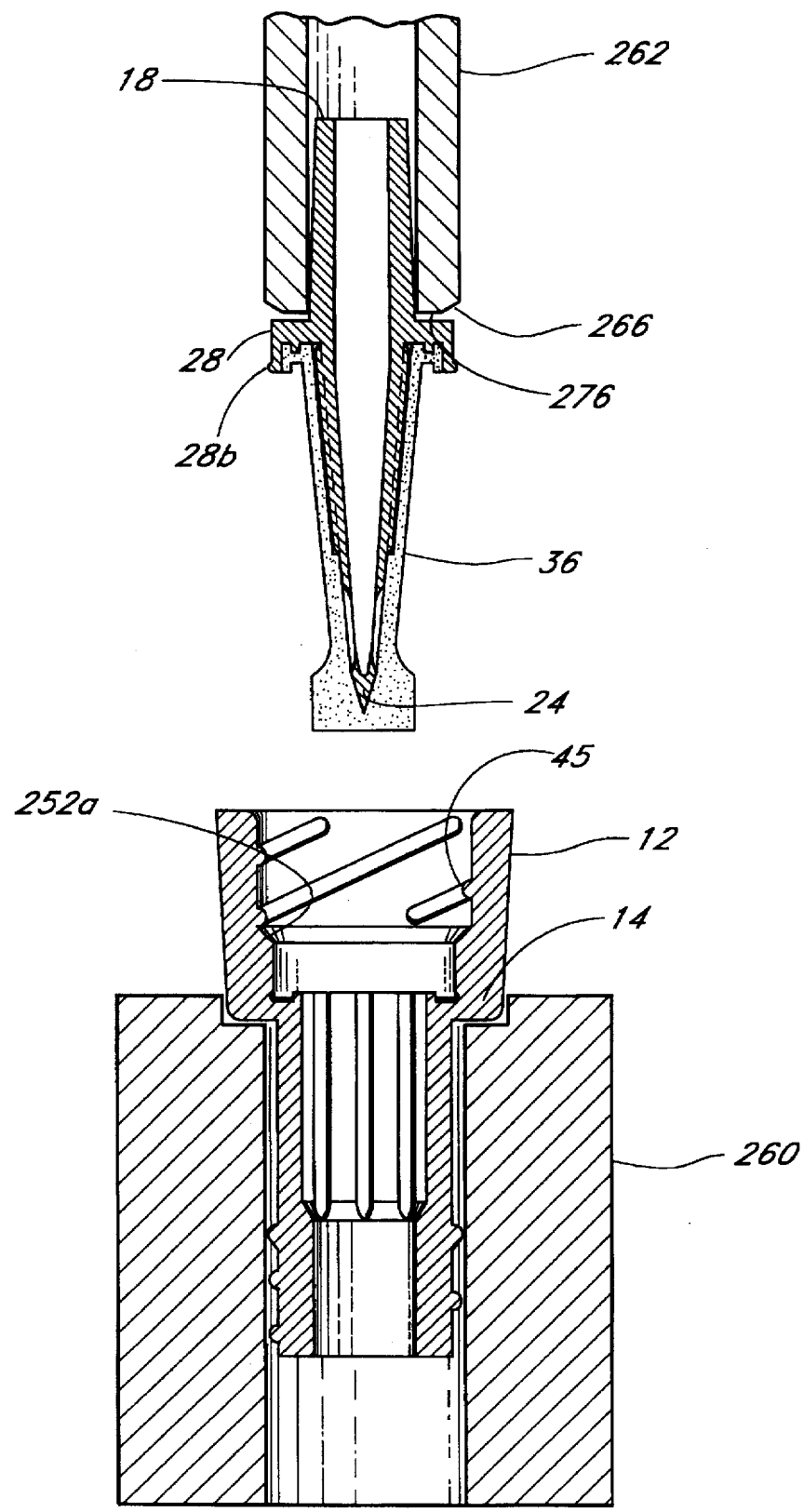
FIG. 28 is a longitudinal cross-sectional view of the components of the assembled valve of FIG. 25, before assembly, inserted with the gouging bit and base of FIG. 26.
Figure 29:
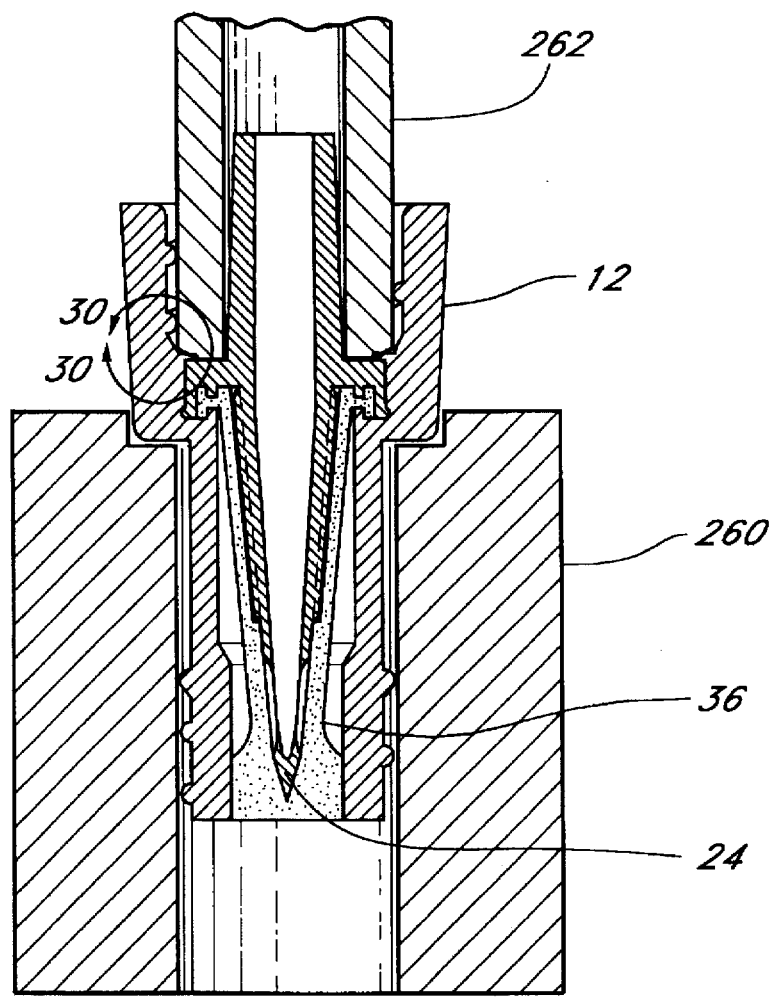
FIG. 29 is a longitudinal cross-sectional view of the assembled valve of FIG. 25, along with the gouging bit and base of FIG. 26.
Figure 30:
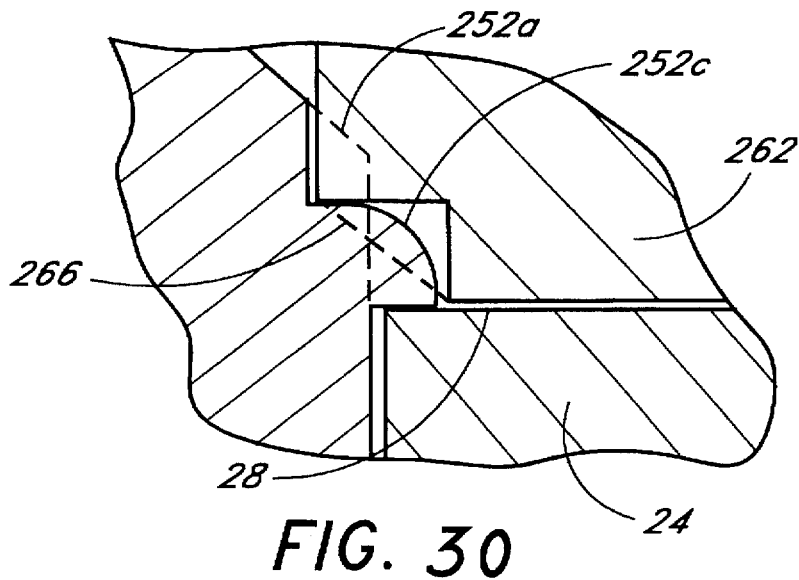
FIG. 30 is an enlarged view of the area inside line 30—30 of FIG. 29.

FIGS. 28, 29, and 30 illustrate the use of the gouging bit 262 and the base 260 to perform the improved method to assemble an improved valve 11 of the present invention. Referring to FIG. 28, a seal 36 of FIG. 3 is placed onto a spike element 24 of FIG. 3. The inner conduit 18 of the spike element 24 is placed inside the bore 298 in the gouging bit 262. The spike element 24 can be retained inside the gouging bit 262 by friction between the outer surface of the inner conduit 18 of the spike element 24 and the inner surface of the bore 298 of the gouging bit 262, or by other appropriate means.

Preferably, the contact surface 276 of the gouging bit 262 contacts the upper surface 305 of the annular cuff 28 of the spike element 24. It is noted that the gouging bit 262 is sized such that the gouging edge 266 extends beyond the outside perimeter of the spike element 24, including the annular detent 28b.

The valve housing 12 shown in FIG. 23 is placed inside of the hole 268 located in the base 260, with the distal end of the housing 11 protruding from the base 260. Once the gouging bit 262 and the base 260 are positioned so that their centers are in direct vertical alignment, the base 260 is moved upwardly, toward the gouging bit 262 (although, as one skilled in the art will recognize, alternately, the bit 262 may be moved downwardly of the seal 36 is secured between the internal lip 27 of the housing 12 and the annular cuff 28 of the spike element 24 to secure the seal 36 inside the housing 12. The annular cuff 28 of the spike element 24 is secured against the underside of the seal lip 42 of the seal 36 by the retaining tabs 252c to secure the spike element 24 and the seal 36 inside the housing 12. The retaining tabs 252c preferably consist of a portion of the material that, before assembly, constituted either the gouging surface 252a of FIG. 23 or FIG. 24. These tabs 252c constitute material from the gouging surface 252a which has been gouged away from its original position on the housing 12 and forced against the lower surface of the annular cuff 28. The retaining tabs 252c are rigid enough to hold the spike element 24 and the seal 36 against the underside of the annular ring 14 of the housing 12 and prevent leakage of fluid through the improved medical valve 11. The spike element 24 is further prevented from removal from the housing 12 because of the annular detent 28b on the annular cuff 28, whereby the detent 28b snaps into the annular groove 14b of the annular ring 14.

The securing force provided by the retaining tabs 252c reduces the need for friction or interference fit between the external portion of annular cuff 28 and the inner surface 254 of annular ring 14, as described above with respect to the first method of assembly. Thus, the outside diameter of the annular cuff 28 can be reduced relative to the inside diameter of the annular ring 14, without allowing leakage to occur within the medical valve 11. For example, it has been found that the outside diameter of the annular cuff 28 can be as little as about 0.003" larger than the inside diameter of the ring 14 and still provide a proper seal. The ability to reduce the diameter of cuff 28 (in relation to the diameter of the ring 14) reduces the possibility that the housing 12 will crack in response to hoop stress, even when the spike element 24 expands because of the conduction of lipids, or other fats through the spike 24. Further, the lessened importance of providing exact tolerances between the annular cuff 28 and the annular ring 14 allows for variations in towards the base 260). As the base 260 approaches the gouging bit 262, the base 260 forces the housing 12 around the outside of the spike element 24 and the seal 36, so that the spike element 24 and the seal 36 penetrate the housing 12. Continued movement of the base 260 causes the housing 12 to be pushed up around the spike element 24 and the seal 36 until the distal portion of the annular ring 14 of the housing 12 makes contact with the annular cuff 28 of the spike element 24, as shown in FIG. 29.

Referring again to FIG. 28, the inside diameter of the housing 12 (including the threads 45) is sufficiently large enough that when the housing 12 is pressed around the outside of the spike element 24 and the seal 36, the annular detent 28b of the spike element 24 passes by the protruding threads 45 and the gouging surface 252a of the housing. Further, the inside diameter of the housing 12 is sized such that the gouging edge 266 of the gouging bit 262 also does not contact the threads 45.

However, the housing 12 and bit 262 are sized such that the gouging edge 266 of the gouging bit 262 does make contact with the housing 12 at the gouging surface 252a. In this manner, the gouging edge 266 of the gouging bit 262 gouges a portion of the gouging surface 252a away from the inner surface of the housing 12. The portion of the gouging surface 252a that is partially separated from the housing 12 is folded or crushed in towards the center of the gouging bit 262 and down toward the annular cuff 28 of the spike element 24 between pairs of ribs 297 by the guiding surfaces 292, 294 and 296 to form a number of retaining tabs 252c, as shown in FIGS. 29 and 30. At this point, the housing 12, the spike element 24, and the seal 36 have been assembled to form an improved medical valve 11, with the retaining tabs 252c securing the spike element 24 and the seal 36 inside the housing 12. The gouging bit 262 can then be separated from the base 260, and the assembled medical valve 11 can be removed.

Figure 32:
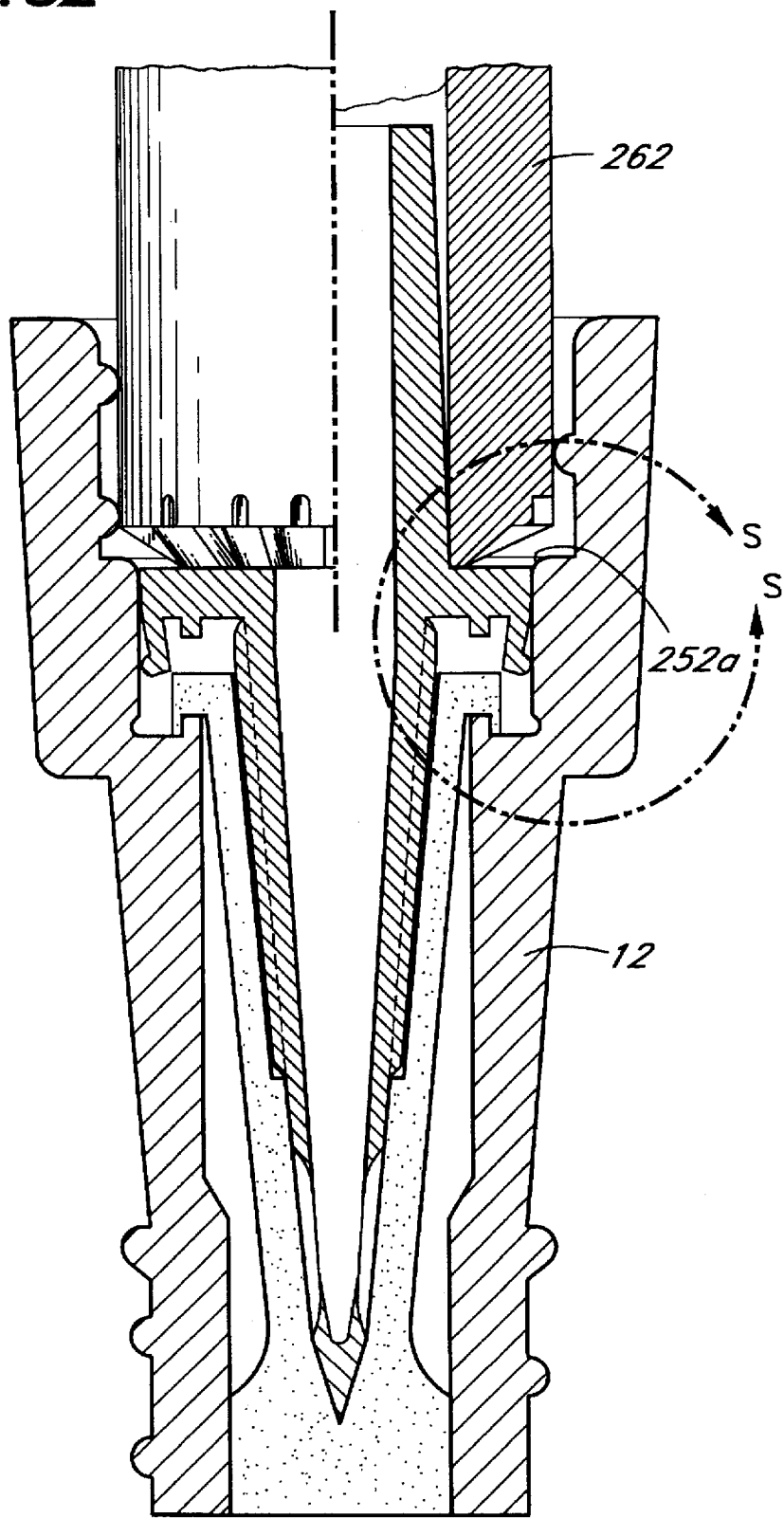
FIG. 32 is a longitudinal cross-sectional view of the components of the assembled valve of FIG. 25, before assembly, with the gouging bit of FIG. 26.

The deformation of the gouging surface 252a to form retaining tabs 252c is further shown in FIGS. 32–35. FIG. 32 illustrates the valve of FIG. 25 prior to assembly. The bit 262 has not yet made contact with the gouging surface 252a of the housing 12.

Referring to FIG. 33, which is an enlarged cross-sectional view taken through line S—S of FIG. 32, it is apparent that the bit 262 has not yet made contact with the gouging surface 252a of the housing 12 of the valve 11. Further along in the process of the manufacture of the valve 11, the bit 262 contacts the gouging surface 252a of the body 12 of the valve 11, as shown in FIG. 34.

Still further in the manufacturing process, the bit 262 deforms the housing 12 of the valve 11 forming the retaining tab 262c. Once the retaining tabs 262c have been created and the bit 262 removed, the spike 24 and seal 36 are advantageously retained within the housing 12 of the valve 11 such that fluid may not leak through the valve 11.

The method described above is the preferred method of assembly for the improved medical valve 11 of the present invention. However, this improved method of assembly can be modified in numerous ways without departing from the essential teachings of the present invention. For example, a bit could be created which deforms a portion of the annular ring 28 of the spike 24 such that tabs are created extending from the annular ring of the spike into the housing of the valve.

Referring again to FIGS. 26 and 27, the tip of the gouging bit 262 comprises a number of surfaces 276, 266, 292, 294 and 296 that combine to perform three basic functions. First, the contact surface 276, which is preferably an annular surface having a diameter of less than the outer diameter of the bit 262, presses against the annular cuff 28 of a spike element 24 to drive the spike element 24 into the housing 12. Second, the gouging surface 266 on the gouging bit 262 scrapes a portion of the gouging surface 252a of the housing 12 away from the remainder of the gouging surface. Specifically, gouging surface 266 is created by the intersection of surfaces 292 and 294 of the gouging bit 262 with the outside surface 291 of the gouging bit 262 to form a relatively sharp edge at the perimeter of the gouging bit 262. Third, the gouging bit 262 folds the gouged material from the gouging surface toward the center of the gouging bit 262 along surfaces 292, 294 and 296. In order to perform this guiding function, surfaces 292, 294 and 296 all preferably slope downwardly and inwardly towards the contact surface 276. Further, in order to create thick retaining tabs as opposed to a thinner retaining ring, ribs 297 are used to guide and separate the gouged material. Each rib 297 thus partially extends from the gouging edge 266 to the guiding surface 276. As illustrated, twelve ribs 297 are advantageously used to create twelve tabs 252c.

FIGS. 26 and 27 illustrate the presently preferred embodiment of the gouging bit 262. However, a person of skill in the art can modify the design of the gouging bit 262 in numerous ways without departing from the teachings of the present invention.

Figure 31:
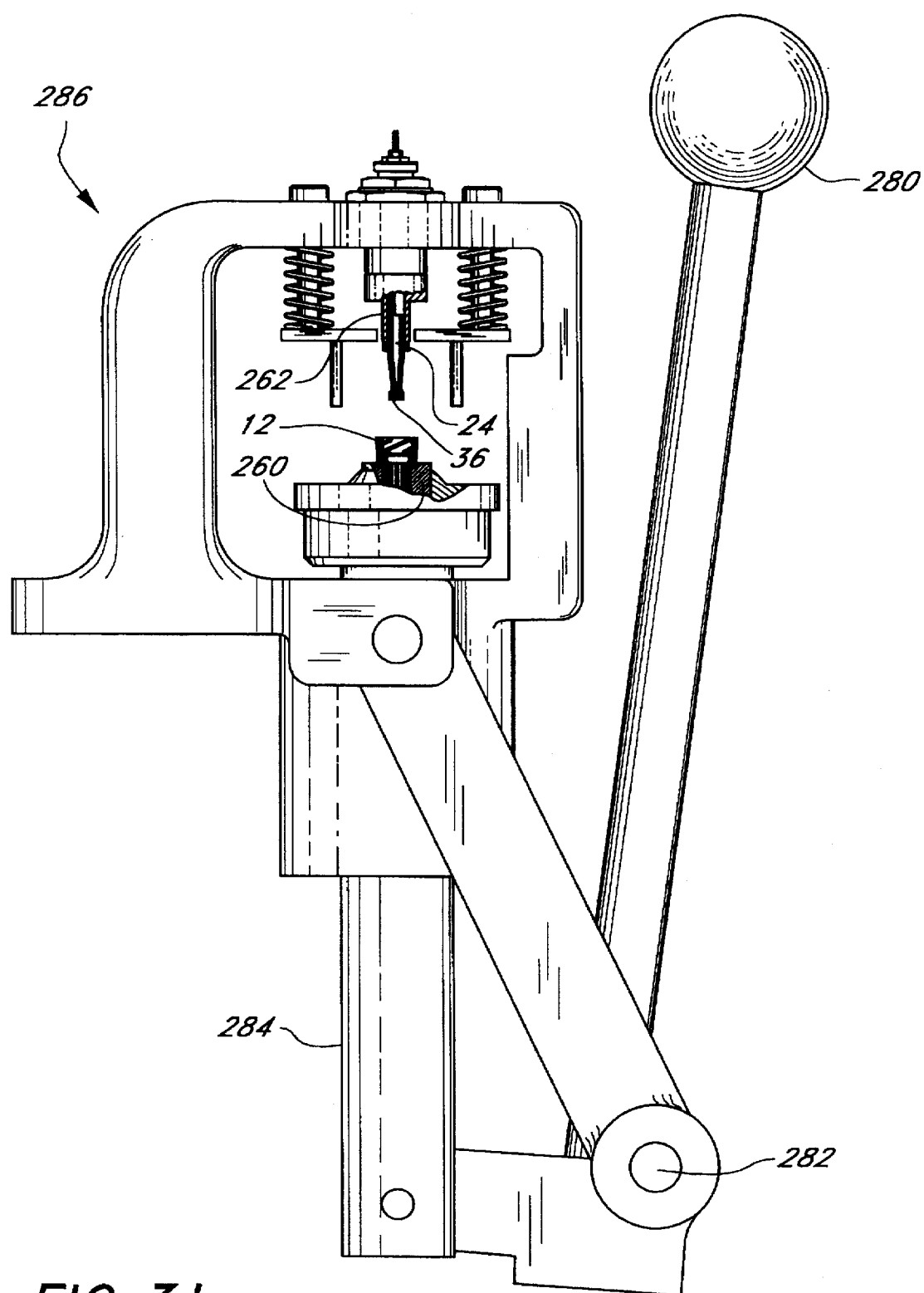
FIG. 31 illustrates a partial cross-sectional view of a manually operated punch machine for using the gouging bit and base of FIG. 26 to perform the second assembly method on the valve components shown as illustrated in FIG. 28.

Substantial force is required to drive the base 260 toward the gouging bit 262 with sufficient force to insert the spike element 24 into the housing 12 and to gouge the gouging surface 252a of the housing 12 and create the retaining tabs 252c. Preferably, therefore, this assembly is accomplished through use of a machine 286. FIG. 31 illustrates the manually operated punch machine 286 that is preferably utilized, along with the gouging bit 262 and the base 260, to perform the improved method of assembly. The punch machine 286 illustrated in FIG. 31 is well-known to a person of skill in the art, and merely incorporates the specific bit 262 and base 260 described above. When utilizing this machine 286, the gouging bit 262 is positioned in the punch machine 286 so that it is in direct vertical alignment with the base 260. Again, the seal 36 is placed over the spike element 24, which is placed inside the gouging bit 262. The valve housing 12 is placed inside the base 260. The punch machine 286 is operated by manually pulling down on a handle 280 to create rotational motion in an axle 282, which in turn creates vertical motion in a piston 284. The vertical motion of the piston 284 is then communicated to the base 260. Thus, by this machine 286, a downward motion in the handle 280 is translated into an upward motion in the base 260 with respect to a stationary bit 262.

Movement of the piston 284 pushes the base 260 in which the valve housing 12 is located upwardly until the annular cuff 28 of the spike element 24 contacts the annular ring 14 of the housing 12. During this procedure, the gouging edge 266 of the gouging bit 262 gouges a portion of the gouging surface 252a away from the inner surface of the housing 12 to create the retaining tabs 252c. A mechanical stop (not shown) is preferably used to prevent the base 260 from being driven too far relative to the gouging bit 262.

After the components of the medical valve have been assembled, the handle 280 is released and returned to its normal position as shown in FIG. 31. At this time, the base 260 also returns to its normal position, also shown in FIG. 31. The completed valve 11 is then removed from the machine 286.

Although FIG. 31 illustrates a manually-operated punch machine, a person of skill in the art will recognize that a wide variety of machines could be designed to implement the improved method of assembly, including an automated version of the machine 286 described above.

The valve 10 or 11 may also be manufactured through the use of glue, spin welding, ultrasonic bonding or snap interference fit. Initially, glue could be placed between the annular cuff of the spike and the housing in order to prevent leakage of fluid through the valve. Further, by rapidly spinning either the housing or the annular cuff of the spike during manufacture, friction between the rapidly moving parts of the spike and housing results in a strong bond being created between the spike and the housing. Finally, the spike, seal and housing of the valve could be bonded through the use of ultrasonic bonding or any of a number of snap interference fit arrangements. In one such arrangement, the tabs 252c can be formed integrally with the spike to create an interference fit.

Operation

The valve 10 or 11 is used to provide a closed, patient access system for transferring a predetermined amount of medication from a remote source to the patient. The valve 10 or 11 is connected by the distal end to the patient, for example, a vein or artery in fluid communication with the valve. Blood fills the valve, but the seal 36d, for example, prevents any blood from leaking from the valve. The delivery end or nose 48 of the medical implement is inserted into the valve as depicted in FIG. 8, pushing the nose 48 against the seal to compress the seal sufficiently to allow the tip 32 of the spike 24 to pierce or penetrate the seal and enter said delivery end. The predetermined amount of medication in its entirety may now be transferred through the nose 48, through the valve 10 or 11 and into the patient. Because, as discussed above, the valve 10 or 11 has very little dead space, transfer of essentially the entire predetermined amount of medication from the syringe 46 through the valve 10 or 11 to the patient is accomplished. Upon withdrawing the nose 48 from the valve 10 or 11, the seal 36d returns to the decompressed state to close the valve 10 or 11 and maintain a fluid tight seal even at high pressures and after repeated uses.

Scope of the Invention

Although the valve of the present invention has been described primarily in the context of its medical application, it will be readily apparent to one having ordinary skill in the art that the valve can be readily implemented in other contexts. For example, the valve can be used in various environments where frequent connections are made, but, contamination from outside cannot be tolerated. Thus, for example, the valve can be used in the food industry to maintain a sanitary connection.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A method of assembling a valve, said valve comprising a spike, a seal, and a body having a cavity therein, said method utilizing a punch machine comprising a gouging bit, a base, and means for pressing said gouging bit and said base together upon operation of said punch machine, said method comprising the steps of:

placing said seal on a first end of said spike;

inserting a second end of said spike inside an opening in said gouging bit of said punch machine, so that said spike is retained in said gouging bit;

inserting said body into said base of said punch machine, so that said body is retained in said base; and operating said punch machine to perform the following steps:

moving said gouging bit and said base together whereby said spike and said seal thereon is pressed into said body;

gouging a surface of said body with a gouging edge of said gouging bit to create at least one tab to secure said spike and said seal thereon inside said body, generally as inserted therein, to produce an assembled valve; and removing said assembled valve from said punch machine.

2. The method of claim 1, wherein said spike includes a hole in fluid communication with a fluid passageway, said seal is resilient, said seal placed over one end of said spike to cover said hole therein, and said body includes a passageway for fluid transmission therethrough.

3. The method of claim 1, wherein the step of moving said gouging bit and said base together involves holding said gouging bit in place and moving said base toward said gouging bit.

4. The method of claim 1, wherein the step of moving said gouging bit and said base together involves holding said base in place and moving said gouging bit toward said base.

5. The method of claim 1, wherein the steps of pressing said spike, with said seal thereon, into said body and gouging a surface of said body are performed simultaneously.

6. The method of claim 1, wherein the steps of pressing said spike with said seal thereon, into said body and gouging a surface of said body are performed during one continuous motion of said base toward said gouging bit.

7. The method of claim 1, wherein said step of operating said punch machine additionally performs the step of folding said gouged material against a surface of said spike to press said spike and said seal against an opposing surface of said body.

* * * * *